(12) United States Patent
Hilson et al.

(10) Patent No.: US 6,881,579 B2
(45) Date of Patent: Apr. 19, 2005

(54) SAMPLE PROCESSING APPARATUS AND METHODS

(75) Inventors: Richard O. Hilson, Sunnyvale, CA (US); Edward P. Donlon, San Jose, CA (US); Donald J. Schremp, San Jose, CA (US); Laurence R. Shea, San Francisco, CA (US); Carol T. Schembri, San Mateo, CA (US); Joseph P. Fredrick, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 372 days.

(21) Appl. No.: 09/919,073

(22) Filed: Jul. 30, 2001

(65) Prior Publication Data

US 2003/0032191 A1 Feb. 13, 2003

(51) Int. Cl.[7] ..................... G01N 35/02; G01N 33/50
(52) U.S. Cl. ..................... 436/47; 422/63; 422/64; 422/65; 422/66; 422/67; 422/100; 436/43; 436/49; 436/86; 436/93; 436/94
(58) Field of Search ................... 422/63–67, 100; 436/43, 47, 49, 86, 93–94

(56) References Cited

U.S. PATENT DOCUMENTS 3,533,744 A * 10/1970 Unger ..................... 436/63
3,832,135 A * 8/1974 Drozdowski et al. ......... 436/47

(Continued)

FOREIGN PATENT DOCUMENTS

EP 549759 * 7/1993

OTHER PUBLICATIONS

Stark, et al., J. of Immunological Methods; 107:89–92; An Automated Device for Immunocytochemistry; 1988.

Primary Examiner—Arlen Soderquist

(57) ABSTRACT

Apparatus and methods are disclosed for processing samples on the surface of supports that are contained in support housings. Biopolymer features are attached to the surfaces of the supports. An apparatus comprises an input element, a holding device for holding a plurality of support housings, one or more fluid dispensing stations, and an output element. Each of the support housings contains a support having attached thereto a plurality of biopolymer features. The holding device is movably mounted with respect to other components of the apparatus. The holding device is adapted to receive a support housing from the input element. The output element is adapted to receive a support housing from the holding device. The apparatus is adapted to index each support housing for a predetermined operation. In use, each of the support housings is moved to one or more processing stations by means of the movable holding device. The location and identity of each of the support housings is indexed. Fluid is applied to the surface of each of the supports at the processing stations to process the samples. Each of the support housings is moved away from the fluid dispensing stations, and fluid is physically removed from each of the supports within the support housings.

43 Claims, 22 Drawing Sheets

U.S. PATENT DOCUMENTS

| | | | |
|---|---|---|---|
| 4,427,294 A | * 1/1984 | Nardo | 356/344 |
| 4,483,927 A | * 11/1984 | Takekawa | 436/43 |
| 4,495,149 A | * 1/1985 | Iwata et al. | 422/65 |
| 4,643,879 A | * 2/1987 | Hanaway | 422/104 |
| 4,720,463 A | * 1/1988 | Farber et al. | 435/286.5 |
| 5,055,408 A | * 10/1991 | Higo et al. | 436/48 |
| 5,266,272 A | * 11/1993 | Griner et al. | 422/104 |
| 5,320,808 A | * 6/1994 | Holen et al. | 422/64 |
| 5,332,549 A | * 7/1994 | MacIndoe, Jr. | 422/63 |
| 5,585,068 A | * 12/1996 | Panetz et al. | 422/64 |
| 5,595,707 A | 1/1997 | Copeland et al. | 422/64 |
| 5,650,327 A | 7/1997 | Copeland et al. | 436/46 |
| 5,985,214 A | * 11/1999 | Stylli et al. | 422/65 |
| 6,093,574 A | 7/2000 | Druyor-Sanchez et al. | 436/180 |
| 6,114,122 A | * 9/2000 | Besemer et al. | 435/6 |
| 6,238,910 B1 | 5/2001 | Custance et al. | 435/287.2 |
| 6,261,523 B1 | * 7/2001 | Schembri | 422/102 |
| 6,352,861 B1 | 3/2002 | Copeland et al. | |
| 6,391,623 B1 | 5/2002 | Besemer et al. | |
| 6,420,169 B1 | 7/2002 | Read et al. | |
| 6,422,249 B1 | 7/2002 | Certa et al. | |
| 2002/0006359 A1 | * 1/2002 | Mathies et al. | 422/100 |
| 2002/0174884 A1 | * 11/2002 | Certa et al. | 134/22.18 |

* cited by examiner

| FIG. 13A | FIG. 13B |

SAMPLE PROCESSING APPARATUS AND METHODS

BACKGROUND OF THE INVENTION

This invention relates to apparatus for processing samples. More particularly, the present invention relates to automated apparatus and methods for washing supports carrying biological material such as polynucleotides. The invention has particular application to the area of analyzing the results of hybridization reactions involving nucleic acids.

Determining the nucleotide sequences and expression levels of nucleic acids (DNA and RNA) is critical to understanding the function and control of genes and their relationship, for example, to disease discovery and disease management. Analysis of genetic information plays a crucial role in biological experimentation. This has become especially true with regard to studies directed at understanding the fundamental genetic and environmental factors associated with disease and the effects of potential therapeutic agents on the cell. Such a determination permits the early detection of infectious organisms such as bacteria, viruses, etc.; genetic diseases such as sickle cell anemia; and various cancers. This paradigm shift has lead to an increasing need within the life science industries for more sensitive, more accurate and higher-throughput technologies for performing analysis on genetic material obtained from a variety of biological sources.

Unique or polymorphic nucleotide sequences in a polynucleotide can be detected by hybridization with an oligonucleotide probe. Hybridization is based on complementary base pairing. When complementary single stranded nucleic acids are incubated together, the complementary base sequences pair to form double stranded hybrid molecules. These techniques rely upon the inherent ability of nucleic acids to form duplexes via hydrogen bonding according to Watson-Crick base-pairing rules. The ability of single stranded deoxyribonucleic acid (ssDNA) or ribonucleic acid (RNA) to form a hydrogen bonded structure with a complementary nucleic acid sequence has been employed as an analytical tool in molecular biology research. An oligonucleotide probe employed in the detection is selected with a nucleotide sequence complementary, usually exactly complementary, to the nucleotide sequence in the target nucleic acid. Following hybridization of the probe with the target nucleic acid, any oligonucleotide probe/nucleic acid hybrids that have formed are typically separated from unhybridized probe. The amount of oligonucleotide probe in either of the two separated media is then tested to provide a qualitative or quantitative measurement of the amount of target nucleic acid originally present. In surface-bound DNA arrays, this separation is typically accomplished by washing the unbound and non-specifically bound material away from the array surface. The resulting wash protocol is normally optimized to the specific requirements of the assay, the probe type, the surface selected and other considerations. The surface is then scanned for the presence of the target.

Direct detection of labeled target nucleic acid hybridized to surface-bound polynucleotide probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be microarrays created by in-situ synthesis or oligonucleotide deposition. Microarrays created by cDNA deposition are used to analyze gene expression patterns and perform genome scanning. Protein arrays are very useful for determining the presence and quantity of specific proteins in a cell or tissue. These arrays may have either proteins or aptamers bound to the surface. Due to the large number of genes in the human genome and other mammals and plants and the large number of proteins created, it is desirable to automate this hybridization process on microarrays.

In one approach, cell matter is lysed, to release its DNA, mRNA or protein which are then separated out by electrophoresis or other means and amplified, if necessary and then tagged with a fluorescent or other label. The resulting mix is exposed to an array of oligonucleotide, cDNA, aptamer or protein probes, whereupon selective binding to matching probe sites takes place. The array is then washed and interrogated to determine the extent of hybridization reactions. In one approach the array is imaged so as to reveal for analysis and interpretation the sites where binding has occurred.

Biological assays involving fluorescently labeled molecules or scattering structures to detect, quantify or identify target chemical species bound to surfaces often use optical detection and imaging systems. Arrays of different chemical probe species provide methods of highly parallel detection, and hence improved speed and efficiency, in assays. These arrays are, for example, DNA arrays and protein matrix arrays, which need to be scanned to measure the number densities of labeled molecules and hence the concentration of target or probe molecules in solution. This sensing process often is accomplished by means of a fluorescence imaging system. Chemiluminescence and radioisotopes are alternative methods commonly employed.

As mentioned above, usually a mosaic of different probes are individually localized to discrete, known areas of a surface of a support. The support may be utilized and analyzed directly or the support may be part of a package, which houses the support. For example, hybridization arrays may be part of a self-contained package. After a hybridization process occurs on the surface of the support, the surface must be washed to remove the unbound and non-specifically bound sample. In a self-contained microarray package, for example, the test sample in the package needs to be washed in order for the features of the microarray to stand out during the detection process such as a scanning process. During the washing process, it is important for the washing protocol be followed precisely in order to remove any excess sample from the actual surface without damaging or destroying the microarray on the surface of the support or causing the hybridized material to melt off the array, thus losing much or all of the signal obtained during the hybridization process.

SUMMARY OF THE INVENTION

One embodiment of the present invention is an apparatus comprising an input element, a holding device for holding a plurality of support housings, one or more processing stations such as, for example, fluid dispensing and optionally removal stations, and an output element. Each of the support housings contains a support having attached thereto a plurality of biopolymer features. The holding device is movably mounted and is adapted to receive a support housing from the input element. The output element is adapted to receive a support housing from the holding device. The apparatus is adapted to index each support housing for a predetermined operation. Optionally, the apparatus may comprise a removal station for removing a cover on a support housing and a drying station for drying the surface of supports in the support housings.

Another embodiment of the present invention is an apparatus comprising an input element, a circuitous transport for holding a plurality of covered packages, each of which contains a support, an element for identifying each of the packages, an element for accessing the package, one or more fluid dispensing, and optionally fluid removal, stations, a device for physically removing unbound materials from the surface of a support within each of the packages, the device being adapted for receiving a package from the holding device, and an output element. The surface of each of the supports has attached thereto a plurality of polynucleotide or protein features. The input element comprises a plurality of package holders such as, for example, shelves, and may be adapted for temperature control. The output element comprises a plurality of package holders, for example, shelves, and is adapted to receive a package from the holding device. The circuitous transport may be, for example, a circular tray that is movably mounted on a frame. The circuitous transport is adapted to receive a package from the input element and adapted to index each package for a predetermined operation.

Another embodiment of the present invention is a method for processing a plurality of samples, each of which are present on a support contained within a support housing. The surface of each of the supports comprises a plurality of biopolymer features. Each of the support housings is moved to one or more fluid dispensing stations. The location and identity of each of the support housings is indexed, preferably continuously indexed. Fluid is applied to the surface of each of the supports at the fluid dispensing stations to process the samples. Fluid is aspirated from each of the supports at the fluid dispensing stations. Each of the support housings is moved away from the fluid dispensing stations, and residual fluid is physically removed from each of the supports within the support housings. Fluid may be removed at the same fluid dispensing station or at a fluid dispensing station that is different from which it is applied.

Another embodiment of the present invention is a method for processing a plurality of samples each of which are present on a support contained in a covered package. The surface of each of the supports comprises a plurality of polynucleotide features. Each of the covered packages is moved from an input element to a movable holding device for holding a plurality of the covered packages. The input element provides for temperature control of the packages. The location and identity of each of the covered packages is indexed, preferably continuously indexed. The holding device is moved in an indexed manner to move the covered packages to a device for removing covers from the covered packages. The holding device is then moved in an indexed manner to deliver each of the packages to one or more fluid dispensing stations. The holding device delivers each of the packages to a device for physically removing unbound materials from the surface of each of the supports. The fluid dispensing and removal station may be one station. The holding device may optionally deliver each package to a drying station. The holding device is moved in an indexed manner to deliver each of the packages to an output element.

Another embodiment of the invention is an apparatus comprising an input element mounted on a frame; a circular tray for holding a plurality of packages, each of which contains a support; a device, mounted on the frame, for reading an identification code on each of the packages; a device, mounted on the frame, for removing a cover on each of the packages; one or more fluid dispensing stations mounted on the frame and adapted to dispense fluids to, and aspirate fluids from, the supports in the packages on the circular tray; a device adapted to remove unbound materials on the surface of a support within each of the packages, the device being mounted on the frame and adapted for receiving a package from the circuitous transport; an output element mounted on the frame and adapted to receive a package from the circuitous transport; and a microprocessor-based or microcontroller-based module connected to a plurality of electrical interface modules for controlling the above devices and elements. The input element and the output element comprise a plurality of shelves. The input element is adapted for temperature control. The surfaces of the supports have attached thereto a plurality of polynucleotide features. The circular tray is movably mounted on the frame and is adapted to receive a package from the input element and adapted to index each package for a predetermined operation.

Another embodiment of the present invention is an apparatus comprising a frame; an input element affixed to the frame; a holding device for holding a plurality of support housings; one or more fluid dispensing stations affixed to the frame; and an output element affixed to the frame. The output element is adapted to receive a support housing from the holding device. The various elements and devices are each controlled by a plurality of microprocessor-based or microcontroller-based modules, each comprising an individual architectural design with different software. The individual architectural design and the software are adapted specifically to manage particular control aspects of the apparatus. The modules are interconnected by a multi-channel shared bus originating at and supervised by a system controller, which interfaces with a front panel display and operator controls. The holding device is adapted to receive a support housing from the input element and adapted to index each support housing for a predetermined operation. The holding device is movably mounted on the frame. Each of the support housings contains a support having attached thereto a plurality of biopolymer features.

Another embodiment of the present invention is an apparatus comprising a frame; an input element affixed to the frame; a holding device for holding a plurality of support housings; one or more fluid dispensing stations affixed to the frame; and an output element affixed to the frame. The output element is adapted to receive a support housing from the holding device. The various elements and devices are each controlled by a plurality of microprocessor-based or microcontroller-based modules, each comprising an individual architectural design and software. The individual architectural design and the software are adapted specifically to control the electromechanical portions of the apparatus that each of the modules serves. The modules are interconnected by a multi-channel shared bus originating at and supervised by a central system controller, which interfaces with a front panel display and operator controls. The holding device is adapted to receive a support housing from the input element and adapted to index each support housing for a predetermined operation. The holding device is movably mounted on the frame. Each of the support housings contains a support having attached thereto a plurality of biopolymer features.

Another embodiment of the invention is a method of exposing an array of biopolymers to a fluid wherein the array is contained in a housing having a cover. The cover of the housing is removed to expose an opening in the housing and fluid is applied to the array through the opening.

DETAILED DESCRIPTION OF THE INVENTION

Figure 1:
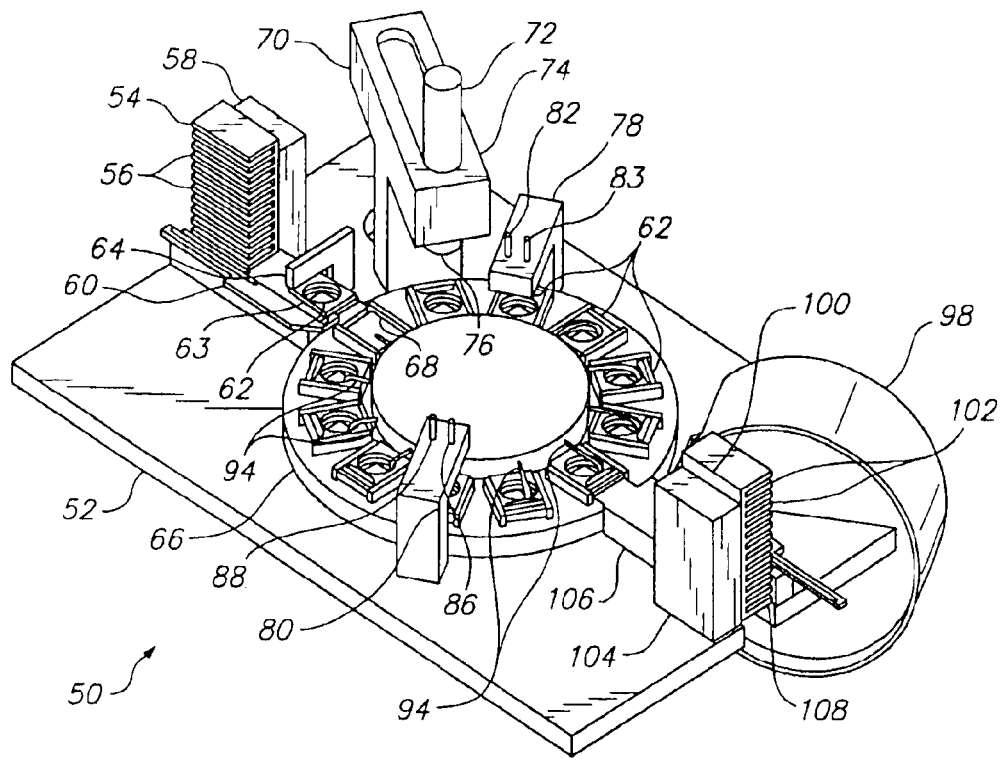
FIG. 1 is a diagrammatic sketch showing in perspective an embodiment of an apparatus in accordance with the present invention.
Figure 2:
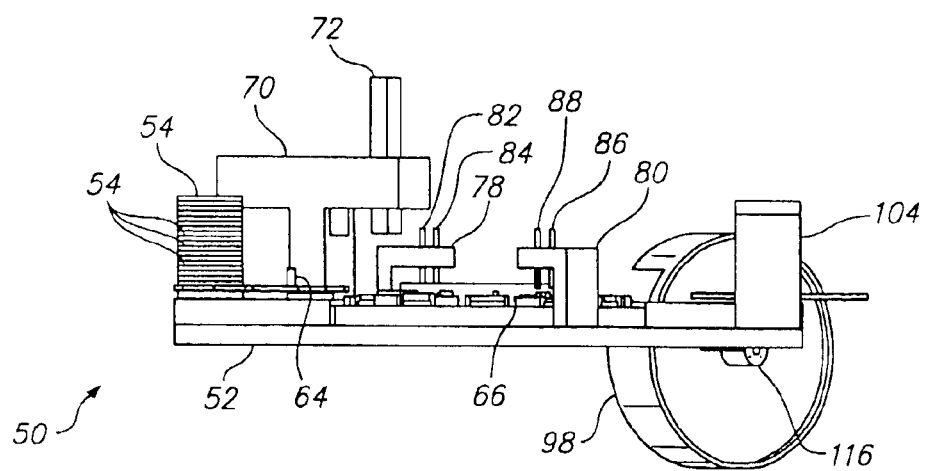
FIG. 2 is another view from a different perspective of the embodiment of the apparatus of FIG. 1.
Figure 3:
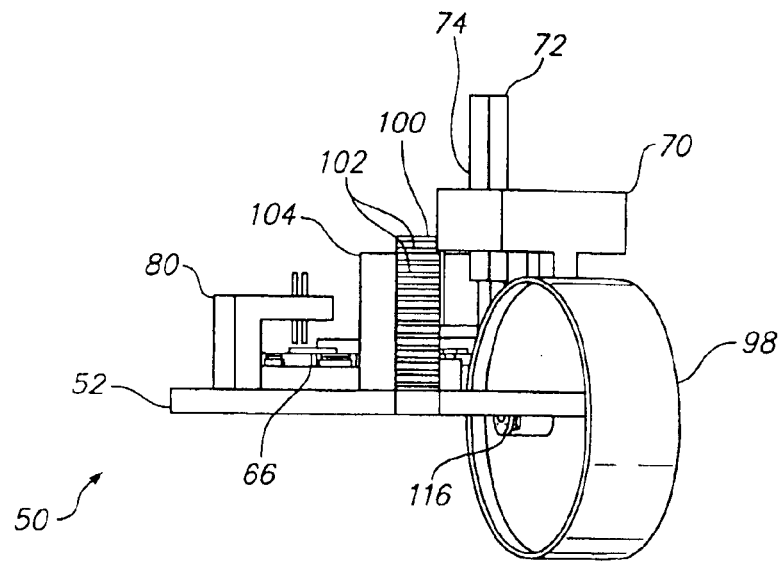
FIG. 3 is another view from a different perspective of the embodiment of the apparatus of FIG. 1.

The present apparatus permit support housings to be moved into positions at which processing of samples on the surface of supports may be accomplished. The surface of each support has biopolymers attached thereto. The supports are contained within the housings. The present apparatus operates in a substantially different manner than many known apparatus involved in the processing of biopolymers on the surface of supports confined within housings. In the present apparatus the support housings are not kept at fixed positions and processing stations moved to and from the area of the housings. Rather, the support housings are moved to processing stations that are in predetermined fixed positions.

Support Housing

As mentioned above, the support is within a support housing. The housing typically includes a body having a reaction cavity disposed therein. In one embodiment, the support is mounted over the cavity on the body such that the front side of the support, i.e., the side upon which biopolymers are attached, is in fluid communication with the cavity which contains the fluid sample and in one embodiment forms the remaining wall of the cavity which contains the fluid sample. The bottom of the cavity may optionally include a light absorptive material, such as a glass filter or carbon dye, to prevent impinging light from being scattered or reflected during imaging by detection systems. In some approaches to which the present invention may be applied such as, for example, supports have either been reacted with labeled, light sensitive target polynucleotides, or have such materials present on the surface. Care to prevent excess light from impinging on these light sensitive dyes should be taken from the time of introduction into the support housing through the steps of incubation hybridization, removal of unbound substances, washing and drying.

The housing usually further comprises fluid inlets and fluid outlets for flowing fluids into and through the cavity. A septum, plug, 2- or 4-part duck-bill valve or other seal may be employed across the inlets and/or outlets to seal the fluids in the cavity. In addition to the fluid inlets and outlets, the housing typically comprises an opening for accessing the interior of the cavity. This opening is sealed with a cover as discussed hereinbelow.

In a preferred embodiment the other side of the cavity is removed. This is essentially a lid or cover, which is removed early in the process such as prior to washing and the like. Accordingly, it is physically not present during a subsequent scanning process. This embodiment differs significantly from known support housings in that the support housing is opened for washing. On the other hand, some known support housings are designed for a wet scan and the support housings are not opened. In the embodiment with a removable lid or cover, the removal facilitates an improved washing process and the surface of a support within the housing is dried completely.

Various embodiments of support housings are known in the art and the following discussion is by way of illustration and not limitation. Support housings other than as discussed below are disclosed in U.S. Pat. No. 6,114,122, the relevant disclosures of which are incorporated herein by reference.

In one format, the support is provided as part of a package, in which the biopolymers are disposed on a first side of a glass or other transparent substrate, which is disposed within the support housing. The substrate is fixed (such as by adhesive) to a support housing with the reactants facing the interior of a chamber formed between the substrate and housing. The housing is usually covered to provide for access to the interior of the housing. An inlet and outlet may be provided to introduce and remove sample to and from a chamber within the housing during use of the support.

Figure 18:
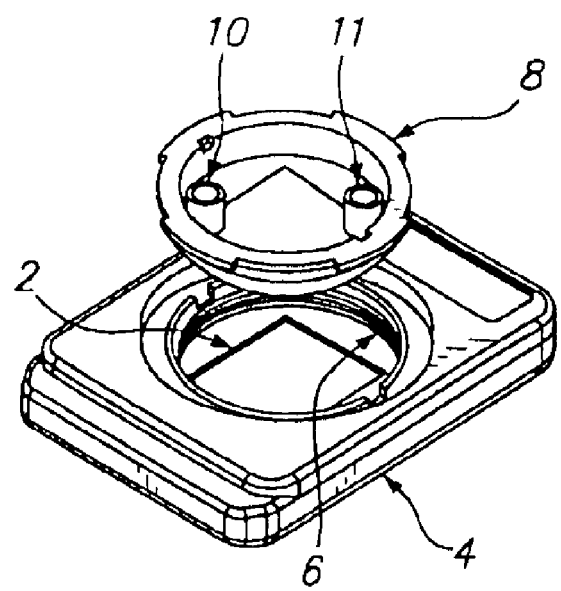
FIG. 18 is a diagrammatic sketch showing a support housing with lid containing two septa.

In another format described in U.S. patent application Ser. No. 09/299,976 filed Apr. 27, 1999, Adjustable Volume Sealed Chemical-Solution-Confinement Vessel, the relevant disclosure of which is incorporated herein by reference, a support substrate 2 is embedded within a plastic base 4 with a continuous inner sidewall 6 to form a well above the surface of the support, reference FIG. 18. A lid 8 with two cylindrical aperture housings 10, 11 orthogonal to the plane of the lid is fitted to a first position within the plastic base, directly above and parallel with the surface of the support to create a small, sealed chamber above the surface of the support. A small volume of sample solution can be introduced into this enclosed chamber via a first needle passing through a septum within a first cylindrical aperture housing, 10. A second needle is inserted through the septum sealing a second cylindrical aperture housing 11 to vent the enclosed chamber, allowing the sample solution to spread across the surface of the support via capillary action. Suction may be applied to the second needle to draw the sample solution across the surface of the support, and pressure can be applied to the sample solution by means of a pump such as, e.g., a syringe pump and so forth, attached to the first needle.

In an alternate embodiment of the above, a single cylindrical aperture housing is incorporated into the lid. Sample solution is introduced into the enclosed chamber by means of a needle inserted through a septum covering the aperture, and the adjustable-volume, sealed chemical-solution-confinement vessel is then spun in a centrifuge to distribute the sample solution across the surface of the support by centrifugal force. After binding of labeled molecules within the sample solution to molecules bound to the surface of the support, the lid can be retracted away from the surface of the support to a second position, resulting in a sealed chamber of a much larger volume above the surface of the support. The larger enclosed chamber facilitates removal of the sample solution from the surface of the support in accordance with the present invention.

In an alternative embodiment of the above, the lid of either design can be physically removed to expose a well with the array located at the bottom. Fluid can be applied directly to the well and removed by aspiration.

Figure 19:
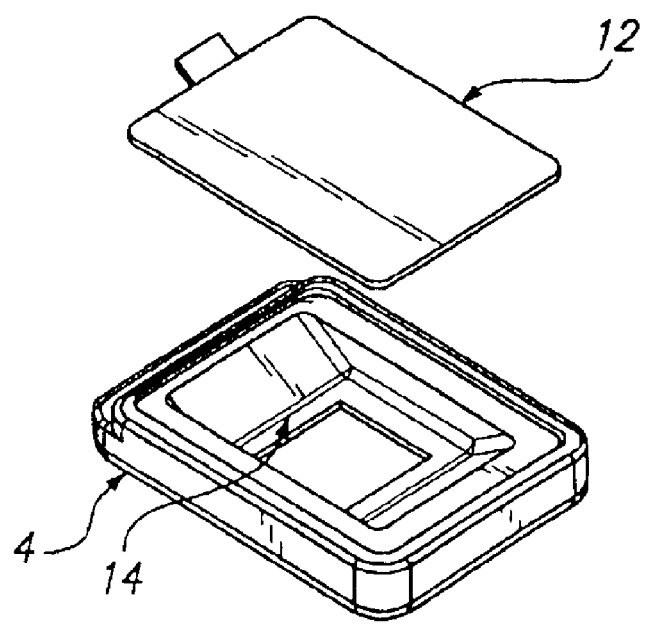
FIG. 19 is a diagrammatic sketch showing a support housing with flexible peel-back lid cover.

In another alternative embodiment, FIG. 19, a solid cylindrical lid in one of the previously described embodiment is replaced with a re-sealable, flexible, pliable film 12 such as plastic or metal-foil film, which is attached to, and covers one face of, the support housing 4. This lid closes off the large enclosed chamber, 14. Sample solution is introduced into this enclosed chamber by peeling-back the pliable film cover 12 and pipetting directly into the enclosed chamber. The film is re-sealed and the support housing is incubated to bind labeled molecules within the sample solution to molecules bound to the surface of the support. After binding, the film can be peeled away from the surface of the support to facilitate removal of the sample solution from the surface of the support in accordance with the present invention. The film is peeled back and discarded in a manner similar to that on, for example, a dairy product container.

The support to which a plurality of biopolymers is attached is usually a porous or non-porous water insoluble material. The support can have any one of a number of shapes, such as strip, plate, disk, rod, particle, and the like. The support can be hydrophilic or capable of being rendered hydrophilic or the support may be hydrophobic. The support is usually glass such as flat glass whose surface has been chemically activated to support binding or synthesis of biopolymers such as polynucleotides, glass available as Bioglass and the like. However, the support may be made from materials such as inorganic powders, e.g., silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; ceramics, metals, and the like. Preferably, the support used in a packaged array is glass, plastic or some other non-porous material. Binding of oligonucleotides to a support or surface may be accomplished by well-known techniques, commonly available in the literature. See, for example, A. C. Pease, et al., *Proc. Nat. Acad. Sci. USA*, 91:5022–5026 (1994).

The apparatus and methods of the present invention are particularly useful in the area of chemical processing of arrays of biopolymers. The present invention allows automation of wet chemical processing steps that typically occur in arrays of biopolymers. Currently, the wet chemical processing is conventionally performed by human laboratory technicians. Human involvement introduces variability and errors from fatigue and the like into the processing protocol. The apparatus and methods of the present invention circumvent fatigue and can operate continuously for long periods of time without degradation in uniformity and the like. The present invention reduces or eliminates process variability and minimizes errors since its operation is mechanically consistent and the actions of the mechanism are algorithmically controlled. The invention provides greater uniformity in executing chemical processing steps often associated with arrays of biopolymers.

A biopolymer is a polymer of one or more types of repeating units relating to biology. Biopolymers are typically found in biological systems (although they may be made synthetically) and particularly include peptides and polynucleotides, as well as such compounds composed of or containing amino acid analogs or non-amino acid groups, or nucleotide analogs or non-nucleotide groups, polysaccharides, and the like. The term polynucleotide includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. The term peptide includes proteins and polypeptides and so forth.

An array includes any one, two or three dimensional arrangement of addressable regions bearing a particular biopolymer such as polynucleotides, associated with that region. An array is addressable in that it has multiple regions of different moieties, for example, different polynucleotide sequences, such that a region or feature or spot of the array at a particular predetermined location or address on the array can detect a particular target molecule or class of target molecules although a feature may incidentally detect non-target molecules of that feature.

The apparatus and methods of the present invention are particularly useful in the area of chemical processing of oligonucleotide arrays for determinations of polynucleotides. In the field of bioscience, arrays of oligonucleotide probes, fabricated or deposited on a surface of a support, are used to identify DNA sequences in cell matter. Additionally, they are used to detect and quantify gene expression by detecting mRNA. The arrays generally involve a surface containing a mosaic of different oligonucleotides or sample nucleic acid sequences or polynucleotides that are individually localized to discrete, known areas of the surface. In one approach, multiple identical arrays across a complete front surface of a single substrate or support are used. However, the arrays produced on a given substrate need not be identical and some or all could be different. Each array may contain multiple spots or features and each array may be separated by spaces. Each feature, or element, within the molecular array is defined to be a small, regularly shaped region of the surface of the substrate. The features are arranged in a regular pattern. Each feature within the molecular array may contain a different molecular species, and the molecular species within a given feature may differ from the molecular species within the remaining features of the molecular array. A typical array may contain from about 100 to about 100,000 or more features. All of the features may be different, or some or all may be the same. Each feature may carry a predetermined polynucleotide having a particular sequence or a predetermined mixture of polynucleotides. While arrays may be separated from one another by spaces, and the features may be separated from one another by spaces, such spaces in either instance are not essential.

Ordered arrays containing a large number of oligonucleotides have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be used for conducting cell study, for diagnosing disease, identifying gene expression, monitoring drug response, determination of viral load, identifying genetic polymorphisms, analyze gene expression patterns or identify specific allelic variations, and the like.

Oligonucleotide probes are oligonucleotides employed to bind to a portion of a polynucleotide such as another oligonucleotide or a target polynucleotide sequence. Usually, the oligonucleotide probe is comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. The design, including the length, and the preparation of the oligonucleotide probes are generally dependent upon the sequence to which they bind. Usually, the oligonucleotide probes are at least about 2 nucleotides, preferably, about 5 to about 100 nucleotides, more preferably, about 10 to about 70 nucleotides, and usually, about 20 to about 60 nucleotides, in length.

Polynucleotides are compounds or compositions that are polymeric nucleotides or nucleic acid polymers. The polynucleotide may be a natural compound or a synthetic compound. The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, cosmids, the genomes of biological material such as microorganisms, e.g., bacteria, yeasts, phage, chromosomes, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like. The polynucleotide can be obtained from various biological materials by procedures well known in the art. A target polynucleotide sequence is a sequence of nucleotides to be identified, detected or otherwise analyzed, usually existing within a portion or all of a polynucleotide.

Various ways may be employed to produce an array of polynucleotides on surfaces of supports such as glass, metal, plastic and the like. Such methods are known in the art. One such method is discussed in U.S. Pat. No. 5,744,305 (Fodor, et al.) and involves solid phase chemistry, photolabile protecting groups and photolithography. Binary masking techniques are employed in one embodiment of the above. In another approach ink jet technology may be used to spot polynucleotides and other reagents on a surface as described, for example, in PCT application WO 89/10977. Other methods include those disclosed by Gamble, et al., WO97/44134; Gamble, et al., WO98/10858; Baldeschwieler, et al., WO95/25116; Brown, et al., U.S. Pat. No. 5,807,522; and the like.

Commonly, in polynucleotide detection binding of an oligonucleotide probe to a target polynucleotide sequence is detected by means of a label incorporated into the target. Alternatively, the target polynucleotide sequence may be unlabeled and a second oligonucleotide probe may be labeled. Binding can be detected by separating the bound second oligonucleotide probe or target polynucleotide from the free second oligonucleotide probe or target polynucleotide and detecting the label. In one approach, a sandwich is formed comprised of one oligonucleotide probe, which may be labeled, the target polynucleotide and an oligonucleotide probe that is or can become bound to a surface of a support. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target polynucleotide, allowing the target polynucleotide to hybridize to a surface-bound oligonucleotide probe, washing away the unbound target polynucleotide and detecting the labeled target polynucleotide that remains. Direct detection of labeled target polynucleotide hybridized to surface-bound oligonucleotide probes is particularly advantageous in the use of ordered arrays.

The signal referred to above may arise from any moiety that may be incorporated into a molecule such as an oligonucleotide probe for the purpose of detection. Often, a label is employed, which may be a member of a signal producing system. The label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation and (v) a specific polynucleotide sequence or recognition sequence that can act as a ligand such as for a repressor protein, wherein in the latter two instances the oligonucleotide primer or repressor protein will have, or be capable of having, a reporter molecule and so forth. The reporter molecule can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like.

In the use of supports to which biopolymers such as polynucleotides are attached, a reader such as, e.g., an array reader, often is used to examine the surface of a support for the presence and amount of signal after a reaction has taken place. The interrogation device may be a scanning device involving an optical system. In common optical analysis techniques, a tightly focused or pinpoint laser beam scans the surface of the support in order to excite labels such as fluorophores, which may be present on the surface of the support. For fluorescent label molecules, the laser beam excites the labels. Then, fluorescent emissions from the fluorophores are analyzed by means of an optical measuring device. In a particular embodiment in accordance with the above, a support housing in the output element is inserted into a reader, such as a laser scanner, which has a suitable mounting means for receiving and releasably retaining the holder in a known position. The scanner is able to read the location and intensity of signal such as fluorescence at each feature of an array following exposure to a fluorescently labeled sample such as a polynucleotide-containing sample. For example, such a scanner may be similar to the G2500 GeneArray Scanner or Agilent G2565 Scanner both available from Agilent Technologies, Inc., Palo Alto, Calif. Results from the interrogation can be processed such as by rejecting a reading for a feature which is below a predetermined threshold and/or forming conclusions based on the pattern read from the array such as whether or not a particular target sequence may have been present in the sample.

The results from the analysis of samples may optionally be processed. In this regard the results obtained from the aforementioned examining may be processed by, for example, computer aided data analysis. In addition, the results may be forwarded to a remote location. By the term "remote location" is meant a location that is physically different than that at which the results are obtained. Accordingly, the results may be sent to a different room, a different building, a different part of city, a different city, and so forth. Usually, the remote location is at least about one mile, usually, at least ten miles, more usually about a hundred miles, or more from the location at which the results are obtained. The method may further comprise transmitting data representing the results. The data may be transmitted by standard means such as, e.g., facsimile, mail, overnight delivery, e-mail, voice mail, and the like.

Components of Apparatus of the Invention

The apparatus of the invention usually comprise a frame to which other components of the present apparatus are secured. The frame may be fabricated by, for example, casting, molding, machining, and the like from laminated or reinforced metal, plastic, metal alloy, solid or aggregate stone, and the like. The frame is usually rectangular in shape, such as, for example, a base plate, although other shapes may be employed such as, for example, circular, square, oval, and the like. The dimensions of the frame are not critical and are usually determined on a practical level depending on the shape of the frame and the number of elements thereon. For a rectangular frame, for example, a base plate, the dimensions usually are about 20 to about 50 inches long and about 15 to 35 inches wide. The thickness of the frame should be sufficient to provide necessary stiffness to support the elements of the apparatus that are affixed to the frame. Usually, the frame that is a base plate is about 0.25 to about 6 inches thick, more usually, about 0.1 to about 2.0 inches thick. The dimensions of the frame should be sufficient to support the weight and to maintain the mechanical accuracy of the elements of the apparatus.

It is usually preferred to provide a cover for the frame that will shield the elements of the apparatus. The cover for the apparatus generally permits the user to access the input element and the output element. The other elements of the apparatus usually are inaccessible to the user and preferably shielded from view. To this end a portion of the cover of the apparatus may be opaque so that the user is not able to view these elements. It is often desirable that light not be permitted to enter the apparatus of the invention because certain labels used in the polynucleotide detection systems discussed above are light sensitive. Accordingly, shielding of certain areas within the interior of the apparatus is desirable and may be accomplished, for example, with a cover that does not allow light to enter the areas of concern. In some circumstances, the cover will not permit light to enter any part of the covered portion of the apparatus. Of course, the elements of the apparatus should be accessible for repair and maintenance normally by a trained technician.

The input element acts to bring support housings comprising samples to be processed into the present apparatus. The input element may be attachable to the frame for the purpose of inputting support housings into the present apparatus. In this situation, therefore, the input element is affixed to the frame on a non-permanent basis using engagement means such as, for example, press fit connections, snap fits alignment pins, posts, fingers, tabs; compression clamps, latching pins, retaining springs and removable fasteners and the like. In this embodiment, the attachment of the input element should provide appropriate orientation of the support housings for introduction into the holding device of the present apparatus.

The input element generally is adapted to contain a plurality of support housings in separate compartments, usually, about 1 to about 48 support housings, more usually, about 4 to 24 support housings, preferably about 8 to about 12 support housings. The compartments are adapted to retain the support housings within the input element until each housing is to be transferred to the holding device. To this end suitable retaining means may be, for example, a lip on the front edge of a compartment, a two-position retaining pin or tab dedicated to each compartment, a support frame fitted with covers on 2, 3, 4, or 5 sides; an indexing cover which exposes only a single compartment at a time while covering all others, a compartment that is only accessible when rotated or moved to an opening, spring clips and so forth. The input element, for example, may be a tray or cassette that contains the support housings where the tray or cassette has been used for incubation or other processing of reagents with the polynucleotides on the surface of the supports. The tray may arrange the support housings in a linear or circular form, in either a vertical or horizontal orientation with respect to the frame. The tray may be four-sided or multi-sided polygonal in shape, for example, rectangular, square, circular disk or annular cylinder. Other examples of input elements include a frame with solid, opaque supports on 5 or fewer sides of each support housing; an open frame such as a wire frame or thin beam frame with open space on 5 or fewer sides of each support housing; a 4- or 5-sided bin or trough-like enclosure with solid, opaque walls surrounding the support housings on at least 4 sides in which the support housings are held in position with the force of a spring which compresses the support housings into a closely spaced stack, pick and place robots and so forth.

In one embodiment the input element comprises a plurality of slots and the input element is adapted to move the slots in a predetermined manner to receive a support housing into the apparatus and move the support housing to a holder for the support housing. In a particular embodiment by way of example and not limitation the input element comprises an elevator system, which comprises a plurality of slots such as, e.g., shelves, vertically stacked, i.e., stacked one on top of another. A mechanism is provided that moves the stacked slots vertically so that a support housing may be delivered in a predetermined manner to the holding device of the present apparatus. Such an elevator system may be designed using, for example, cylindrical (round rod) or rectangular guide rails or track to constrain the position of the moving elevated element to two degrees of freedom and, for example, belts, cables, threaded lead screws, pneumatic cylinders, hydraulic cylinders or the like to apply motive force for moving the elevated element. The motive force, thus, may be provided by, for example, electric, pneumatic, or hydraulic means such as, for example, a rotary or linear motor or actuator. In one embodiment, the tray used to hold the support housings during the incubation step is received by the elevator. This embodiment eliminates the need to transfer the support housings individually.

In another approach the input element may be a circular tray such as a carousel or the like having a plurality of compartments for the support housings. A suitable mechanism is included that extracts the support housings from the circular tray and orients the support housings for delivery to the holding device. The circular tray and mechanism may be similar in design to that employed in the Agilent G2565 Scanner. Alternatively, the circular tray may comprise individual compartments that rotate with respect to a wall surrounding the compartments. There is an opening in the wall to permit ingress and egress of each support housing from a compartment by a moving mechanism such as discussed below.

The present apparatus may be designed to provide for monitoring and control of the temperature of the support housings within the present apparatus. In one embodiment the temperature is monitored and controlled in the volume of the apparatus in which the input element is enclosed, particularly when the support housings are present in the input element, while the remainder of the apparatus operates without temperature control at room temperature. A suitable temperature control system operates to maintain the temperature within the apparatus or within the input element at optimized levels predetermined by the chemical processing protocol of the invention or at levels determined by the human operator. The temperature control system maintains a predetermined temperature or temperatures in a range from 0 to 70 degrees C. In one embodiment a thermal source for applying heat energy above room temperature, or the thermal sink for removing heat energy below room temperature for cooling, may be employed adjacent the input element. Thermal sources may apply heat energy by means of conduction from electric resistance elements, semiconductor thermoelectric heat pumps or fluid heat exchangers. Thermal sources may apply heat energy by means of radiation from long wavelength, infrared, radiation sources. Thermal sinks may remove heat energy for cooling purposes, by means of conduction from semiconductor thermo-electric heat pumps, fluid heat exchangers, compressed-gas expansion coolers, mechanical or absorption refrigeration.

In another embodiment, the temperature is monitored and controlled in the structure surrounding the support housings as they reside in the input element and on the support housing holding device in any of their forms, while the remainder of the apparatus operates without temperature control and is nominally at room temperature. A suitable temperature control system operates to maintain the temperature in these structures at optimized levels predetermined by the chemical processing protocol of the invention or at levels determined by the human operator.

In another embodiment the temperature is monitored and controlled in segregated compartments surrounding internal portions of the apparatus including, but not limited to, the input element, cover or lid removal station, first fluid dispensing station, second fluid dispensing station, and holding device. A suitable temperature control system operates to maintain the temperature within each of these compartments at optimized levels predetermined by the chemical processing protocol of the particular use of the apparatus or at levels determined by the human operator.

In other embodiments the temperature is controlled within the elevator at a first temperature, for example, the original hybridization temperature, and the transfer region is held at a second temperature, typically lower than the first temperature, to allow for a controlled cool down of the support prior to commencing the wash procedure.

The tray of support housings can come from the hybridization oven. It may be manually or robotically moved to the input element of the present apparatus. A support housing may be mechanically delivered from the input element to a holding device of the invention. Mechanical delivery involves a suitable arm or other device to move the support housing from a location in the input element to the holding device. Where the input element comprises a vertically stacked plurality of slots, the arm moves each support housing into an appropriate empty slot. As mentioned above, the input element may be a tray such as a carousel that holds a plurality of support housings that have been treated prior to introduction into the apparatus of the invention. The present apparatus is adapted to permit the tray to be attached thereto and the support housings are subsequently moved to the holding device of the present apparatus as discussed above.

As mentioned above, the support housings should be presented to the present apparatus in proper orientation. Accordingly, the input element provides a means to ensure the proper orientation of the support housings delivered to the holding device of the present apparatus. Proper orientation is related to the accessible portion of the support housing, which must be positioned so that components of the various processing stations used to access the support housing are able to interact with the support housing to gain access. An example of the above may be illustrated by way of example and not limitation with reference to one particular embodiment wherein an array is located on the bottom of a support housing in the form of a cup designed to contain a sample and wash fluids. During the processing steps, the cover or lid is removed from the support housing. Since the support housing is now open, it is important that the support housing is oriented with respect to gravity so that nothing spills. The input element feeds the support housings into the apparatus in the proper orientation to facilitate lid removal and subsequent wash and dry steps.

As mentioned above, the support housings are moved to a holding device. This may be accomplished by a moving mechanism such as, for example, a push-pull mechanism that removes the support housing from the input element and moves the support housing to its predetermined position on the holding device. In another approach an arm is employed as the moving mechanism to accomplish the above. Other approaches include a carriage positioned by means of a belt, cable or lead screw actuated by a linear or rotary motor or a non-contact gas-bearing flotation slide, and the like. Such devices for moving items such as the support housings discussed herein are well-known in the art.

The holding device is adapted to hold a plurality of support housings as discussed above for the input element. The holding device is adapted to receive a support housing from the input element and is adapted to index each support for a predetermined operation. The holding device is movably mounted on the frame and serves to move the support housings to the various components of the present apparatus. The holding device may be in any convenient shape or size. One embodiment of a holding device in the present apparatus is a circuitous transport that moves the support housings in a non-linear fashion. For example, the circuitous transport may be a circular tray such as a carousel and the like. The circular tray is rotated to receive each support housing or package from the input element and to move the support housings to the components of the present apparatus. This is by way of illustration and not limitation. The holding device may take any convenient form that will permit support housings to be received from the input element and moved to a location at which the samples on the supports within the support housings may be processed. Accordingly, such holding device may be a linear tray, including an endless belt and the like, which is adapted for lateral movement to present each support housing to a processing station or to the output element of the present apparatus. Other forms for the holding device include a serpentine track with a linked-belt, a conveyer, and the like. The holding device may be movable by virtue of a linear actuator, linear or rotary motor such as a stepper or servomotor, a Geneva mechanism, and the like.

As mentioned above, the input element and the holding device permit each of the support housings to be identified, indexed and tracked. To assist in the identification function, the support housings may comprise an identification code. A suitable reading device is employed for reading the identification code. The reading device is affixed to the frame either directly or through the intermediacy of another element of the present apparatus. The reading device is located usually between the input element and the holding device and is able to read the identification code as the support housings are transferred from the input element to the holding device. Information read from the identification code is fed to the system controller for the apparatus and correlated with the indexed position of the support housing on the holding device. In this way the identity and location of each of the support housings can be tracked and the processing of each support may be linked to the identification of the support. Such information may be loaded into a data storage database for use by other systems.

The identification code is usually placed in a location that does not interfere with the processing of the samples on the supports in the support housings. The identification code may be placed on the outside of the support housing or package. In one embodiment the present apparatus comprises a bar code reader between the input element and the holding device. Appropriate bar codes are placed on the support housings. The bar code may, for example, be printed on an opaque label attached to the front side, or other readable side, of the support housing. Information read from the bar code can be used to identify and index the support housings in an apparatus in accordance with the present invention.

In another approach a metal homing block may be mounted on the holding device. The homing block then moves with the holding device. A metal detector may be mounted on the frame in such a manner that the movement of the holding device brings the homing block in the vicinity of the metal detector at some point in time during the movement of the holding device. A change in signal from the metal detector indicates that the homing block is in a certain position. Accordingly, during each full movement of the holding device the location of a particular support housing is known.

The present apparatus may also comprise an element for accessing the interior of the support housing to process samples on the supports confined therein. Where the support housing or package comprises a cover such as a lid, the element for accessing the support housing is a device for removing, either partially or fully, the cover from the package. The nature of such a removing device is dependent on the nature of the cover for the accessible area of the support housing. The cover may be affixed to the support housing by interference, friction fit or adhesive to enable the cover to be removed. In this embodiment, the cover may be made from the same material as the support housing or from a different material provided that the cover has sufficient strength to be manipulated by the element for accessing the support housing. On the other hand, the cover may be such that the interior of the support housing may be accessed by peeling off or puncturing the cover. In this embodiment the cover typically will be a puncturable or malleable material such as, for example, foil, e.g., a metal foil such as aluminum foil, thin plastic, a plastic-metal laminate, e.g., metallized mylar, a deformable rubber dam or septum, and the like.

Where the support housing comprises a peelable cover, the device for accessing the interior of the support housing is one that is able to grasp and peel away the cover. In one embodiment, for example, a portion of the cover is grasped by the device. In another embodiment, a flap, which extends beyond the support housing is pulled back over the support housing to break a seal such as a heat-seal, adhesive bonded seal and the like. Other such embodiments will be suggested to those skilled in the art in view of the above discussion.

The device for accessing the interior of the support housing may be a pulling device that interacts with the cover and pulls the cover from the support housing or simultaneously rotates and pulls the cover from the support housing. The pulling device may grasp substantially the entire cover or it may grasp only a portion of the cover such as a lip or the like. The pulling device may be a circular device that is formed in a pattern complementary to that of the cover. In this approach, in one rotation the pulling device fits into recesses in the lip of the cover. When the pulling device is rotated, reentrant portions are moved underneath the outer periphery of the cover. In this manner, the pulling device may conveniently move under portions of a lip, ring, tab, flange, or the like. Other such devices for accessing the interior of the support housing include a circular cutting device for cutting an opening in the cover such as a cover made from a metal foil, for example, in order to access the support. In many instances the pulling device should engage the lid in a balanced manner. When the pulling device is raised, the cover is then removed from the support housing.

As mentioned above, the cover may be a puncturable cover, which would not require a separate device for accessing the interior of the housing. Rather, the interior may be accessed by means of a puncturing component of, for example, the processing stations that form part of the present apparatus. Such puncturing component may be, for example, a pin, thin tubing, a syringe or other type of needle, a pipette, a blunt instrument, or the like.

The apparatus of the invention further comprise one or more stations where the samples on the supports within the support housing may be processed. The processing stations may be fixed or movable, preferably fixedly attached to a frame on which the holding device is movably mounted. There may be a number of stations, all of which carry out a different processing function, or there may be two or more stations carrying out the same function together with one or more other stations. Usually, the number of processing stations is about 2 to about 30, more usually about 12 to about 24. Two of more of the same station are desirable where certain processing steps require more time than other steps and permits operation of the present apparatus on a fixed time regimen. Processing includes, by way of illustration and not limitation, washing the supports to remove unbound materials, aspirating materials from the surface of the supports, waste removal from the supports, addition of reagents to the surfaces of the supports, mixing of reagents on the supports, aspirating reagent materials from the surface of the supports, removal of waste reagents from the surface of the supports, and drying of the surface of the supports and the like.

In one embodiment one or more fluid dispensing stations are affixed to the frame. Any fluid dispensing station may be employed that dispenses fluids such as water and aqueous media. The aqueous media may contain buffering agents such as, e.g., borate, phosphate, carbonate, Tris, barbital and the like at pH of about 3 to about 11 and/or polar cosolvents such as oxygenated organic solvents of from 1–6, more usually from 1–4, carbon atoms, including dimethylsulfoxide, alcohols, ethers, formamide and the like. The fluid dispensing station generally comprises a pump for moving fluid, a suitable temperature control system that operates to control the temperature of the fluid at optimized levels, predetermined by the chemical processing protocol of the invention, prior to and during fluid movement. The fluid dispensing station additionally comprises a valve assembly, a manifold and plumbing as well as a means for metering and delivering predetermined quantities of fluid into a support housing. Usually, the fluids to be dispensed are pumped from the dispenser, which may be held at a controlled temperature. In this regard any standard pumping technique for pumping fluids may be employed in the present apparatus. For example, pumping may be by means of a peristaltic pump, a pressurized fluid bed, a positive displacement pump, e.g., a syringe pump, and the like. Particular examples of fluid dispensing stations the Kloehn 50300 or 50810 Syringe Dispensing Module from Kloehn Ltd, Las Vegas, Nev.; the Gilson Inc. model 215 Liquid Handler and those manufactured by Cavro Scientific Instruments, Sunnyvale, Calif., and the like.

It is often desirable to employ fluid dispensing stations that have a dual function of dispensing fluid into the support housings and aspirating fluid therefrom. Suitable aspiration techniques include use of a vacuum, syringe pumping, gravity assisted draining, tip-over dumping, positive displacement pumping, and the like. Usually, the fluid dispensing station will provide the dual function of dispensing liquids through one nozzle and aspirating the fluid by use of the same nozzle or a second nozzle. Alternatively, a needle is employed in which the aspirating fluid travels up a central bore and the dispensed fluid flows down in an outer sheath. In this manner, the needle assembly is self-cleaning. In this embodiment the fluid dispensing station further comprises one of two nozzles for directing the fluid flows, a pump for moving fluids, a suitable temperature control system that operates to control the temperature of the injected fluid at optimized levels, predetermined by the chemical processing protocol of the invention, prior to and during fluid movement, a valve assembly, a manifold and plumbing as well as a means for metering and delivering predetermined quantities of fluid into a support housing.

It should be mentioned that the types of nozzles for the fluid dispensing stations are dependent on the types of covers for support housings discussed above. In particular, syringe or other puncturing type nozzles are employed for covers that are puncturable as discussed above. On the other hand, where the covers are removed either partially or fully from the support housing, other types of blunt, non-piercing nozzles, which are well-known in the art, may be employed.

As mentioned above, processing of the samples may include mixing fluid reagents and wash solutions with the samples on the surface of the supports. Mixing may be accomplished mechanically by agitation such as that achieved by (i) gross mechanical motion of the support housing, for example, rocking, rotating, tilting, orbiting, etc., (ii) vortex mixing through the action of directional gas or fluid flow guided by directional nozzles, (iii) fluid motion through the action of recirculated fluid pumping, (iv) ultrasonically by bulk-material or surface acoustic waves, (v) locally induced bubble formation and deformation through the action of localized heating, (vi) providing constant or intermittent dispensing and removal of wash fluid, and so forth.

In one embodiment for mixing, a processing station of the present apparatus may comprise a plurality of nozzles mounted on a frame attached to the frame. The nozzles are disposed to provide for vortex mixing of materials on the surface of supports within the support housings. To this end the nozzles are adapted to deliver a stream of gas such as air or an inert gas across the surface of the support. The intensity of such a gaseous stream is usually relatively low, usually, about 1 to about 3 pounds per square inch (psi). Accordingly, the nozzles are connected to a suitable pump such as, for example, an air compressor with filter and regulator or gas supply and the like.

In many instances it is often desirable to remove fluids and waste materials and dry the supports subsequent to washing or other processing. Any convenient drying device may be employed that is consistent with the nature of materials on the supports. The temperature for drying should be such as not to damage any sample or other reactants present on the surface of the support. Usually, the supports are dried at a temperature of about 0° C. to about 60° C., more usually, about 25° C. to about 40° C., more usually, at ambient temperature. The drying station may be, for example, a forced-air or inert gas dryer employing an air-knife configuration, a centrifugal-force spin dryer, a vacuum (or inverse-air) knife configuration, blot or squeegee wipe dryer and the like.

In a preferred embodiment the present apparatus may comprise one or more elements for physically removing fluids and waste materials from the surface of supports in the support housing in order to dry such surfaces. This is to be distinguished from merely evaporating fluids from the surface of the support. In this approach, it is important to remember that the drying operation is to remove fluids such as washing buffer/reagents and other waste by-products, not to dry them on the slide. In application of the present invention to biopolymer arrays, there appears to be a significant increase in the background signal during the scan procedure if such fluids are dried onto the support. Accordingly, a force sufficient to provide effective removal of fluids and waste materials is applied at the drying station to the surface of the supports within the support housings. Usually, this process is accomplished at a temperature of about 0° C. to about 60° C., more usually, about 25° C. to about 40° C., more usually, at ambient temperature.

In one embodiment of the above, the station for drying the supports may comprise a stream of gas such as air or an inert gas. The gaseous stream, in the form of a cone from one or more point-source orifices, impinges the surface of the support to physically remove fluids and waste materials.

In another variation, the gaseous stream, in the form of a thin ribbon from a linear orifice, impinges the surface of the support to physically remove fluids and waste materials. The intensity of such a gaseous stream is usually about 20 to about 80 psi, with a flow rate of approximately 10 liters per minute or less. In another approach the station comprises a spin dryer that spins the support housings at a speed sufficient to physically remove fluids and waste materials by centrifugal force. For effective removal of fluids and waste materials from the surface of the supports, the dryer is usually spun at a speed of about 1000 to about 2000 rpm, developing a force of at least approximately 200 g.

The drying station is adapted to receive and return support housings from and to the holding device. To this end moving mechanisms such as discussed above, for example, an arm for moving the support housings or a push-pull mechanism, a conveyor belt, and so forth, may be employed. Such a mechanism extracts a support housing from the holding device and transfers it to the drying station. In the case of the spin dryer, the support housing is transferred to a bucket on the spin dryer rotor. The spin dryer rotates the support housing for a period of time at speeds sufficient to apply approximately 200 g in order to remove excess fluids and waste materials. The drying period may vary from a few ten's of seconds to a few minutes. After drying the support housing, the mechanism transfers the support housing from the drying station back to the holding device.

The apparatus of the present invention further include an output element affixed to the frame. The output element is adapted to receive a support housing from the holding device. To this end moving mechanisms such as discussed above, for example, an arm for moving the support housings or a push-pull mechanism and so forth, may be employed.

The output element may be similar in construction to the input element as described above, with the exception that it is not temperature controlled. In one embodiment the output element may be a tray, such as a carousel and the like, that has a plurality of compartments into which the support housings are loaded. The tray may then be moved to an interrogation area for interrogating the surface of the supports usually for the presence of a signal as discussed above.

The apparatus of the invention further comprise appropriate electrical and mechanical architecture for operation of the various elements of the apparatus and provide for the various components of the apparatus to operate in concert. In this way the input of a support housing to the holding device, the presentation of the support housing to various processing stations, and the output of a support housing from the holding device may be carried out to provide for continuous movement of the support housings into and out of the present apparatus. Such architecture includes, for example, electrical sensors, electromechanical actuators and motors, temperature and motion control electronic circuitry, operator controls and displays, electrical wiring and connections, fluid and pneumatic sensors, actuators, valves and pumps, fluid and gas tubing and plumbing, fluid control electronic circuitry bearings, load sensors, etc., and so forth. Examples of such architecture are discussed below in more detail. The apparatus may also comprise various computer interfaces for controlling the various components of the present apparatus.

Figure 4:
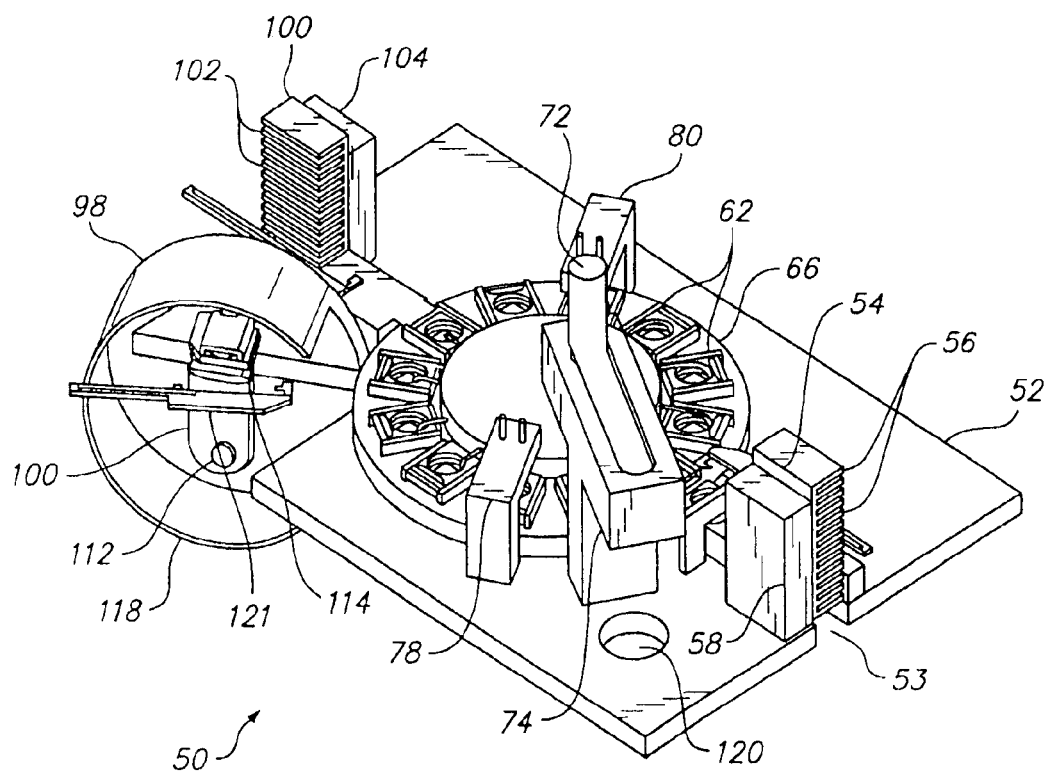
FIG. 4 is another view from a different perspective of the embodiment of the apparatus of FIG. 1.

An embodiment of an apparatus in accordance with the present invention is depicted in FIGS. 1–4. Apparatus 50 comprises a frame 52 having affixed thereto input element 54, which comprises a plurality of shelves 56, mounted mechanism 58, which moves shelves 56 vertically to dispose support housings 62 to push-pull mechanism 60 in a predetermined manner. Shelves 56 are adapted to contain an individual support housing 62. Also mounted on frame 52 is bar code reader 64, under which support housing 62 may pass on its journey to a holding device in the form of carousel 66 having a plurality of compartments 68 for receiving support housings 62 from input element 54. Carousel 66 is rotatably mounted on frame 52. Device 70 for removing cover 63 on support housing 62 is also mounted on frame 52. Device 70 comprises piston 72, which is movably mounted for vertical movement in arm 74 of device 70. Piston 72 has tip portion 76 that is adapted to engage and remove cover 63 from support housing 62. Fluid dispensing stations 78 and 80 are mounted on frame 52 and comprise appropriate pumping elements (not shown). Fluid dispensing station 78 comprises nozzles 82 and 84 for respectively aspirating fluid from, and delivering fluid to, the surface of a support within support housing 62. Likewise, fluid dispensing station 80 comprises nozzles 86 and 88 for respectively aspirating fluid from, and delivering fluid to, the surface of a support within support housing 62. Also mounted on frame 52 through the intermediacy of a suitable frame (not shown) are nozzles 94, which are connected to a pump (not shown). The pump projects a gaseous stream across the surface of a support in support housing 62 to provide mixing of materials thereon. Spin dryer 98 is mounted on frame 52. Referring to FIG. 4, the interior of spin dryer 98 may be seen more clearly. Spin dryer 98 comprises a rotor 110 with an integral counter-balance 112, a support housing bucket 114, spin dryer motor 116, and splash shield 118. Support housing 62 is loaded into bucket 114 by mechanism 121. Drive motor 116 causes the rotor 110 with support housing 62 to accelerate and reach a nominal rotational speed. The resulting centrifugal forces remove the waste residues from the surface of the well of the support housing. Such waste residues are contained and held apart from the rest of the apparatus by splash shield. At the completion of the drying process, support housing 62 is removed from the bucket 114 and transferred via carousel 66 to the output element 100. Output element 100, which is similar in construction to input element 54 is also mounted on frame 52. In that respect output element 100 comprises a plurality of shelves 102 mounted mechanism 104, which moves shelves 102 vertically to dispose support housings 62 to push-pull mechanism 106 in a predetermined manner. To this end frame 52 has opening 108 so that shelves 102 may be moved vertically into position for transferring a support housing 62 into one of shelves 102 by means of push-pull mechanism 106. A similar opening 53 (see FIG. 4) is present in frame 52 for vertical movement of shelves 56 of input element 54.

Operation of Apparatus of the Invention

The operation of an apparatus in accordance with this invention is described next s with reference to FIGS. 1–4. Support housings 62 are placed in shelves 56 of input element 54. When the apparatus of the invention is activated, shelves 56 are indexed by vertical movement by means of mechanism 58 so that the first support housing 62 can be engaged by push-pull mechanism 60. Then, the first support housing 62 is extracted from the shelf and is transferred past bar code reader 64, which reads the bar code on support housing 62. This enables the present apparatus to track the identity and location of the support housing 62 in carousel holding device 66. The support housings remaining in input element 54 are held at a predetermined temperature until cover 63 is subsequently removed. Generally, this temperature is one that preserves the binding reactions involving biopolymers on the surface of a support within support housing 62.

Carousel 66 indexes one position clockwise to device 70 where cover 63 is removed from support housing 62 and is discarded through hole 120 in support plate 22. The interior of support housing 62 is thus rendered accessible.

Carousel 66 then indexes one place clockwise to first fluid dispensing station 78. At this station, nozzles 82 and 84 are lowered near the surface of the support housing 62 containing the biopolymer sample. The sample, which is primarily located on surface of the support in support housing 62, is diluted with wash fluid and then aspirated by means of nozzle 82. A first wash fluid, heated to a temperature equal to the temperature of the support housings held in the Input Element, is injected into the well and onto the biopolymer surface of support housing 62 by means of nozzle 84. The first wash fluid is cyclically injected and aspirated one or more times, over a period on the order of tens of seconds, in order to dilute the sample. After the prescribed dilution period, the first wash fluid is injected again to fill the well of the support housing.

Nozzles 82 and 84 are raised away from the support housing and the carousel 66 is indexed one position clockwise to a location where the mixing of the wash fluid starts. At this location, a stream of air delivered from nozzle 94 blows across the surface of the support on which the wash fluid is found. This stream of air causes vortex agitation and mixing of the wash fluid inside the well of support housing 62. During this mixing process, the mixing fluid and the temperature of the support housing are held at a temperature equal to that of the support housings in the Input Element. After a predetermined period of time, on the order of minutes, carousel 66 is indexed clockwise again to second fluid dispensing station 80. At this location, nozzles 86 and 88 are lowered near the surface of the support housing 62 containing the first wash fluid. The first wash fluid is removed through nozzle 86 of station 80. The second wash fluid, at room temperature or below, is injected by nozzle 86 and aspirated by nozzle 88 from the well of support housing 62. The second wash fluid is cyclically injected and aspirated one or more times, over a period on the order of tens of seconds. After the prescribed period, the second wash fluid is injected again to fill the well of the support housing.

Nozzles 86 and 88 are raised away from the support housing and the carousel 66 is indexed to the next position where nozzle 94 impinges a stream of air on the surface of a support within support housing 62, which agitates and mixes the wash fluid on the surface for a period of time on the order of minutes. During this mixing process, the mixing fluid and the temperature of the support housing are held at a temperature below room temperature. When agitation of the wash fluid is complete, it is aspirated from the support housing leaving the well mostly free of fluids.

Each time carousel 66 indexes clockwise, another support housing 62 is extracted from input element 54 and the bar code is read as discussed above. Eventually, all positions on the surface of carousel 66 are filled with support housings 62.

Then, the first support housing 62 is transferred to spin dryer 98, where the support housing is spun at a sufficient speed and for a time sufficient to physically drive all excess fluid from the surface of the support within support housing 62. Following this step, support housing 62 is extracted from spin dryer 98 and transferred back to the carousel 66. Carousel 66 is then indexed one position clockwise. At this point, push-pull mechanism 106 transfers support housing 62 from carousel 66 to output element 100.

The methods in accordance with the present invention may be carried out under computer control, that is, with one or more embedded computers and an optional external supervisory computer. The embedded computers may be microprocessor- or microcontroller-type, configured with internal central processing units, program and data memory, analog-to-digital and digital-to-analog conversion interfaces, digital input and output (I/O) interfaces suitable for the control tasks required. These embedded computers are driven by custom embedded software specific to the control tasks and operation actions and methods described herein. The software programs provide for coordinated and time synchronized (i) movement of each support housing from an input element to a holding device and from said holding device to an output element, wherein the surface of each of the supports comprises a plurality of biopolymer features and wherein the location and identity of each of the support housings is continuously indexed, (ii) maintenance of prescribed temperatures at varied locations within the apparatus of the invention, (iii) movements of support housings among one or more fixed fluid dispensing stations dispensing and aspirating fluid to the surface of each of the supports at the fluid dispensing stations to process the samples with one or more wash fluids, (iv) movements of the support housings away from the fluid dispensing stations to allow agitation and mixing of wash fluids for a period of time, (v) movements of the support housings between the holding device and the drying station, (vi) manipulation of the support housings in the dryer to physically remove excess fluid and waste materials from each of the supports within the support housings. Such software may be written, preferably, in Visual C++, C/C++ or in processor-specific assembly language.

The external supervisory computer may, for example, be an IBM® or Apple MacIntosh® compatible personal computer (PC). The external computer is driven by software specific to the methods described herein. A preferred computer hardware capable of assisting in the operation of the methods in accordance with the present invention involves a system with the following specifications: Pentium® processor or better with a clock speed of at least 200 MHz, at least 128 megabytes of random access memory at least 1 gigabyte disk mass storage, at least 10 megabit/sec Ethernet LAN interface, running a suitable operating system, either Windows NT 4.0 or Linux (or successors thereof). Supervisory computer software, that may be used to carry out the methods herein, may use C/C++, Visual BASIC, Visual C++, suitably extended via user-written functions and templates.

It should be understood that the above computer information and the software used herein are by way of example and not limitation. The present methods may be adapted to other embedded and supervisory computers, operating systems and runtime application-specific software.

Control Systems

The discussion herein pertains to the underlying embedded control systems that activate and animate the mechanical, pneumatic and fluidic components of the apparatus of the invention causing them to manipulate support housings and reagents with which supports having surfaces comprising biopolymers are contacted. The underlying embedded control systems comprise a collection of electronic circuitry, one or more embedded microprocessors (or microcontrollers) each with suitable interfaces to the mechanism's sensors and actuators, and related embedded control software. Three architectures are described by way of illustration and not limitation. The first, and preferred architecture, represents a highly integrated design in which control is concentrated in a central processor. This architecture consists of a single main microprocessor for primary control of the apparatus supported by an auxiliary diagnostic microprocessor. The main microprocessor connects to a plurality of function-specific interfaces through a microprocessor address/data/control signal bus. These interfaces support serial data communication, operator interaction, motor/actuator control, fluid and pneumatic valve control, barcode reader, thermal heater and cooler control, and analog-to-digital conversion of sensor signals.

The second architecture represents a modular design in which control of the apparatus is distributed among several processors whose actions are supervised by a central control processor. This architecture consists of a plurality of microprocessor-based modules each tailored for the specific control function that the module serves, where both the electrical and embedded software are specifically optimized for the control function. Each microprocessor-based module is dedicated to controlling one aspect of the apparatus of the invention, for example, apparatus-wide motion control or apparatus-wide temperature regulation.

The third architecture represents a modular design in which control of the apparatus is distributed among several processors whose actions are supervised by a central control processor. This architecture consists of a plurality of microprocessor-based modules, each dedicated to controlling all aspects of a particular station, of the apparatus of the invention, for example, Accessing Device Station (70) or Second Fluid Dispensing Station (80). Each of these three architectures is described in detail below.

Control System Architecture 1

The design concept of System Architecture 1 (FIGS. 14–17) is the localization of all apparatus control activities into one single main microprocessor. This processor connects to a variety of peripheral interfaces, which monitor sensor signals and control actuators and motors. The activities of the main processor are augmented by an auxiliary microprocessor, which performs system self-test and diagnostic support. Conditioned power is supplied to the system from a central power supply module, which converts AC mains power to suitable DC power.

System Architecture 1 (FIG. 14) comprises a Main Microprocessor 800 whose address/data/control/serial I/O buses are expanded, by buffer 810, and connected via bus 812 to nineteen function-specific peripheral interfaces 840, 850, 860, 870, 880, 890, 900, 910, 920, 930, 940, 950, 980, 990, 1000, 1020, 1040, 1050 and 1060. Each of these peripheral interfaces is described in the following text. Main Microprocessor 800 has a basic word-length of at least 32-bits and incorporates several on-chip peripherals including multiple general-purpose counter/timers, a real-time interrupt controller, UART (Universal Asynchronous Receiver Transmitter) and SPI (Serial Peripheral Interface) data communication interfaces, memory management controller and an external bus interface. These on-chip peripherals are all part of typical state-of-the-art 32-bit microprocessors. The Main Microprocessor interfaces directly with at least 1024 kilobytes of suitable data RAM memory 806, 512 kilobytes of program ROM memory 804 and 256 kilobytes of boot-ROM memory 802. The program ROM may be constructed from any suitable technology, but are commonly downloadable, re-programmable FLASH type.

A System Diagnostic Microcontroller (FIG. 14) 820, with associated RS-232 serial data communications interface 832, supports apparatus self-test and diagnostics. This 16-bit microcontroller connects to external test systems that direct more rigorous subsystem testing and diagnosis. It communicates with the Main Microprocessor 800 via serial I/O interface line 830. Microcontroller 820 comprises a 16-bit processor 822, with on-chip program ROM memory 824 of at least 64 kilobytes, on-chip data RAM memory 826 of at least 16 kilobytes, on-chip UART & SPI serial I/O interfaces 828, on-chip general purpose digital I/O interface 834, and an IEEE Standard 1149-compatible JTAG scan-bus interface 836. The JTAG scan-bus interfaces to all off-chip system peripheral interfaces via scan-bus lines 838. The internal states of these off-chip peripherals can be examined and altered by diagnostic software through the scan-bus interface and, thus, tested more rigorously than by only sampling their external signal states.

The nineteen function-specific peripheral interfaces that connect to the Main Microprocessor via bus 812 include an Ethernet Interface 840, an instrument Front-panel Interface 850, twelve electric Motor/Actuator Interfaces 860, 870, 880, 890, 900,910, 920, 930, 940, 1040, 1050, and 1060, a Fluid & Pneumatic Valve Interface 950, a Barcode Reader Interface 980, a general-purpose Digital I/O Interface 990 to miscellaneous apparatus sensors and indicators 994, a Thermal Heater/Cooler Control Interface 1000, and an Analog-to-Digital (AID) Interface 1020.

The 10/100-BaseT Ethernet Interface (FIG. 14) 840 provides 10 megabits per second (Mbps) or 100 Mbps serial data communications between the apparatus and any compatible external device or system. Such systems may be, for example, a supervisory control computer or network server. The Ethernet Interface connects to the Ethernet medium 844 via driver 842.

Figure 14:
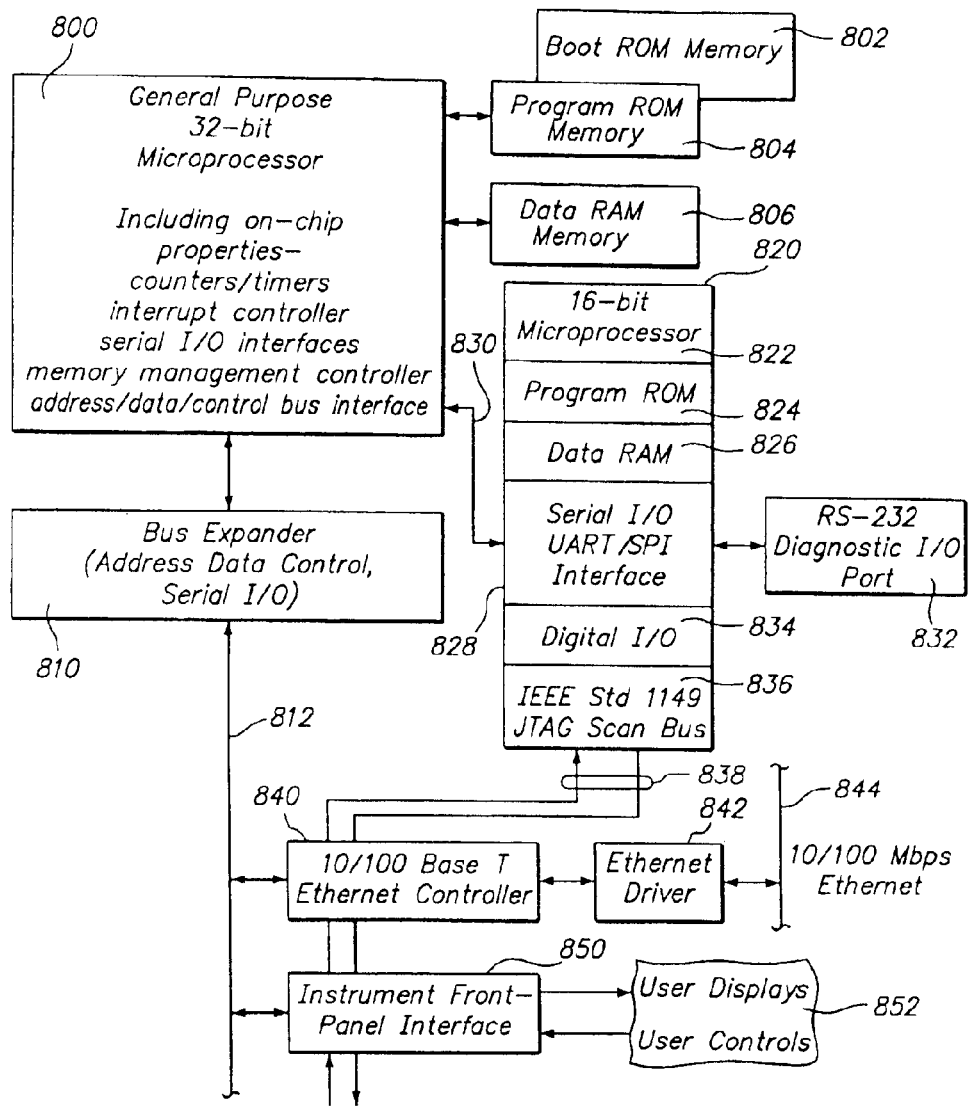
FIG. 14 is a diagrammatic sketch of a portion of another embodiment of a control system architecture for an apparatus in accordance with the present invention illustrating its main microprocessor, memories, diagnostic processor, external I/O interfaces and operator interface.
Figure 15:
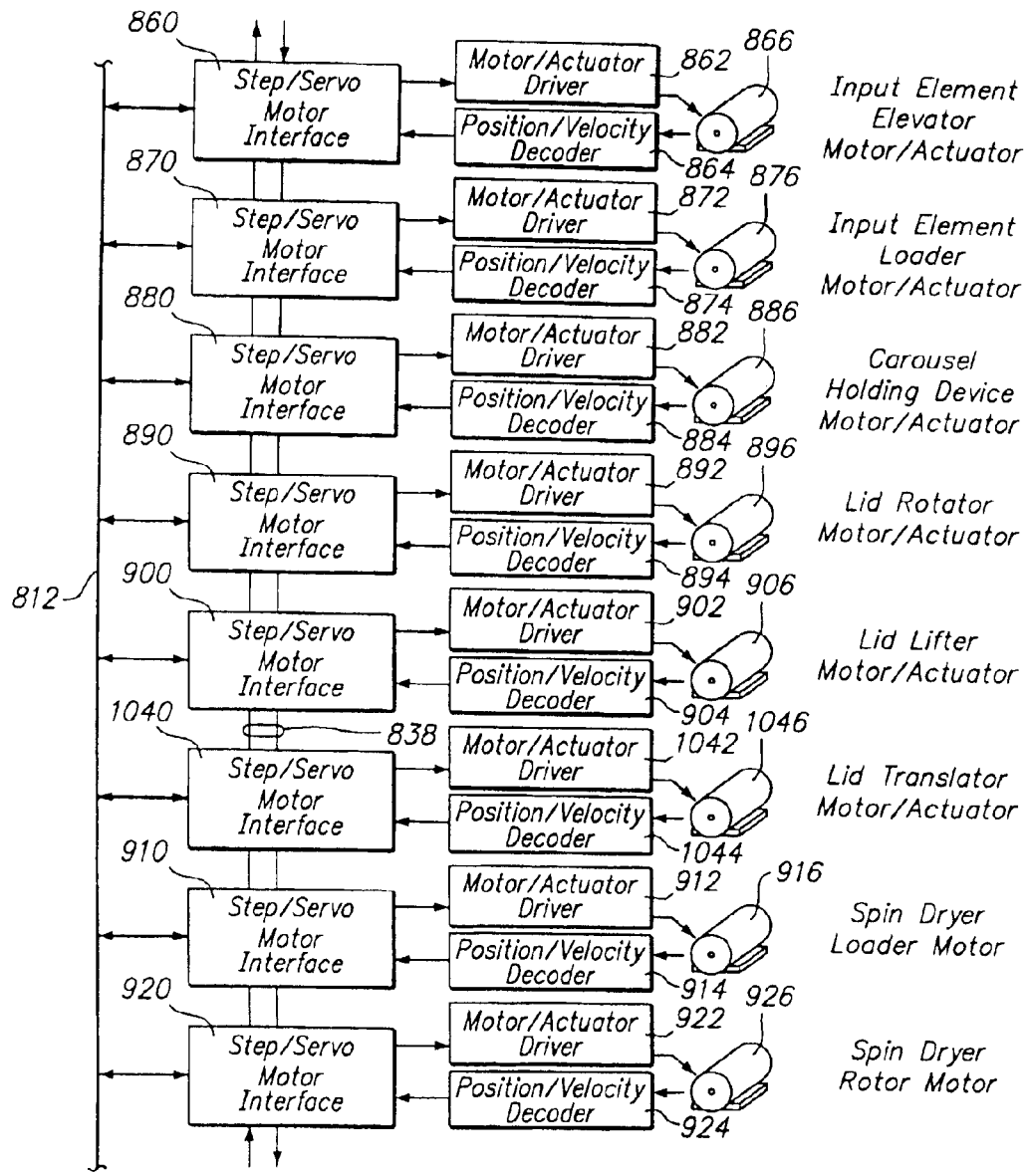
FIG. 15 is a diagrammatic sketch continuation of FIG. 14 illustrating its motor controllers.
Figure 16:
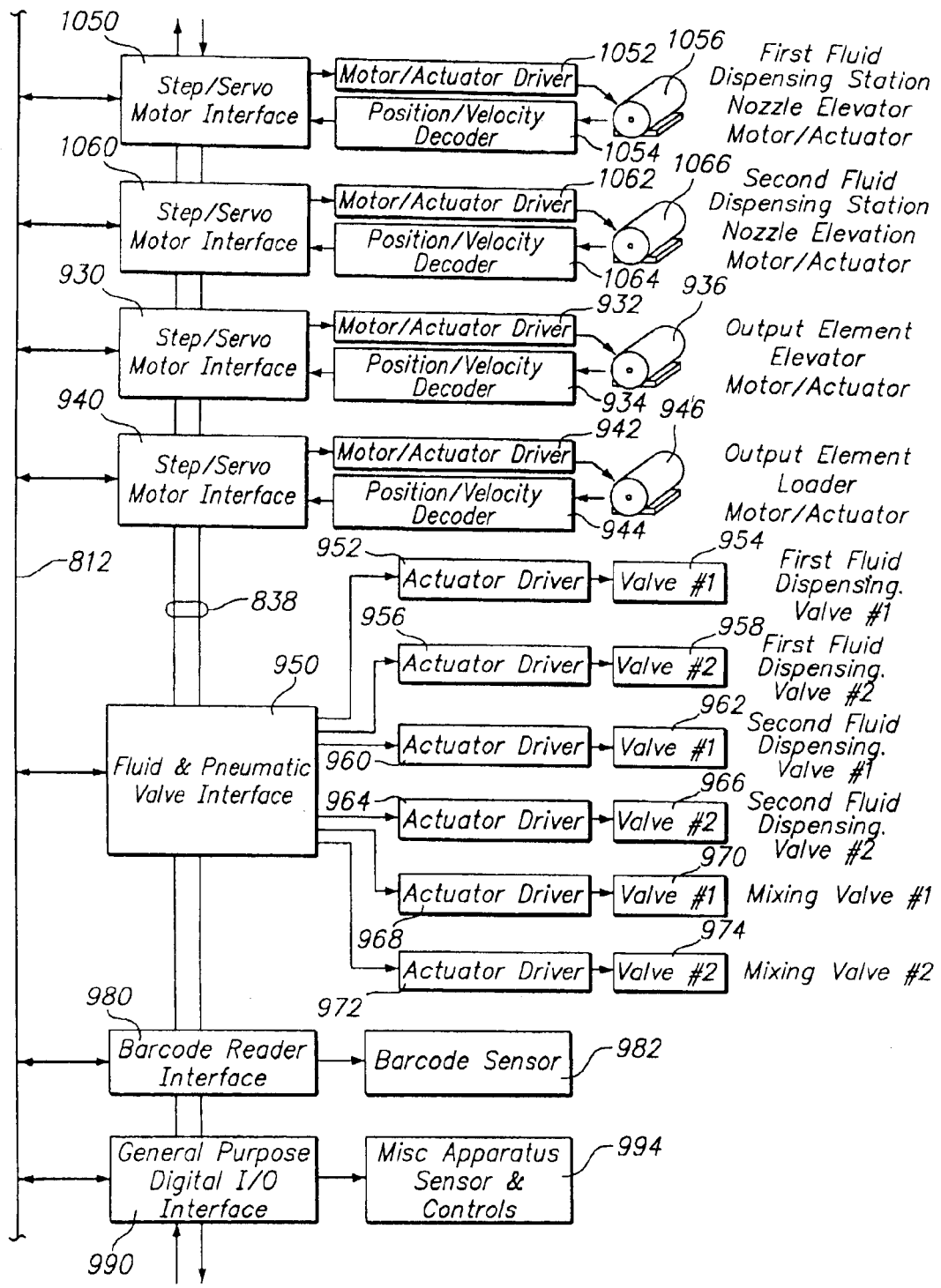
FIG. 16 is a diagrammatic sketch continuation of FIG. 14 illustrating additional motor controllers, fluid interface, barcode reader and general purpose I/O interface.

The user interacts with the apparatus through various Front-panel Displays and Controls 852 (FIG. 14). The displays indicate machine status to the operator. Controls permit the operator to influence the real-time activities of the apparatus. The displays and controls are electrically connected to the Main Microprocessor via interface 850.

Electromagnetic motors and actuators are used to produce some of the mechanical motions of the apparatus. In order to obtain precision position, velocity or accelerating motion control, stepping-type or servo-type motors are used. In this architecture, (FIGS. 15 and 16) there are twelve major mechanical actions that are produced by motors: (1) stepping-servo Motor Interface 860 with associated driver 862 and position decoder 864 controls the Input Element Elevator Motor 866 in order to position a support housing to the plane of the Carousel; (2) stepping-servo Motor Interface 870 with associated driver 872 and position decoder 874 controls the Input Element Loader Motor 876 in order to extract a support housing from the Input Elevator and load it onto the Carousel; (3) stepping-servo Motor Interface 880 with associated driver 882 and position decoder 884 controls the Carousel Holding Device Motor 886 in order to index it to the necessary station positions; (4) stepping-servo Motor Interface 890 with associated driver 892 and position decoder 894 controls the Lid Rotator Motor 896 in order to disengage the support housing's lid; (5) stepping-servo Motor Interface 900 with associated driver 902 and position decoder 904 controls the Lid Lifter Motor 906 in order to remove the support housing's lid; (6) stepping-servo Motor Interface 1040 with associated driver 1042 and position decoder 1044 controls the Lid Translator Motor 1046 in order to discard the support housing's lid through hole 120; (7) stepping-servo Motor Interface 1050 with associated driver 1052 and position decoder 1054 controls the position of the fluid dispensing/aspirating nozzles for the First Fluid Dispensing Station via nozzle elevation motor 1056; (8) stepping-servo Motor Interface 1060 with associated driver 1062 and position decoder 1064 controls the position of the fluid dispensing/aspirating nozzles for the Second Fluid Dispensing Station via nozzle elevation motor 1066; (9) stepping-servo Motor Interface 910 with associated driver 912 and position decoder 914 controls the Spin Dryer Loader Motor 916 in order to transfer a support housing from the Carousel to the Spin Dryer; (10) stepping-servo Motor Interface 920 with associated driver 922 and position decoder 924 controls the Spin Dryer Rotor Motor 926 in order to spin dry the support housing; (11) stepping-servo Motor Interface 930 with associated driver 932 and position decoder 934 controls the Output Element Elevator Motor 936 in order to position it to the plane of the Carousel; and (12) stepping-servo Motor Interface 940 with associated driver 942 and position decoder 944 controls the Output Element Loader Motor 946 in order to transfer a support housing from the Carousel to the Output Elevator. Software, written in processor-specific assembly language or, preferably, in C/C++ executing in the Main Microprocessor monitors the position, velocity and acceleration of these motors and modulates the applied drive levels to maintain control.

The apparatus uses several types of washing fluids in the normal course of its operation. These fluids are applied and removed from the sample support housing via a system of supply tanks, pumps, tubing, valving and waste tanks. Filtered air and/or filtered nitrogen gas are also used in the apparatus to pressurize fluid tanks, move and mix fluids, dry surfaces, and operate motion actuators such as pneumatic cylinders. Gases are applied via a system of pressure sources, pumps, tubing, and valves. Both fluid and pneumatic pumps and valve-actuators are controlled by the Fluid and Pneumatic Interface (FIG. 16) 950. This interface controls the First Fluid Dispensing Stations's valve #1 954 and valve #2 958; the Second Fluid Dispensing Station's valve #1 962 and valve #2 966; and mixing valves #1 970 and #2 974 via drivers 952, 956, 960, 964, 968, 972 respectively. Software, written in processor-specific assembly language or, preferably, in C/C++ executing in the Main Microprocessor controls these valves in accordance with the process protocol of the apparatus.

The Barcode Reader Interface 980 (FIG. 16) with its associated optical sensor 982 scans the barcode attached to each support housing in order to identify it. The barcode pattern is decoded by the interface 980 and communicated to the Main Microprocessor via bus 812.

The apparatus usually incorporates sensors and indicators 994 (FIG. 16) that are useful and necessary for its operation. Control of these indicators and status from these sensors are communicated to the Main Microprocessor via interface 990.

Figure 17:
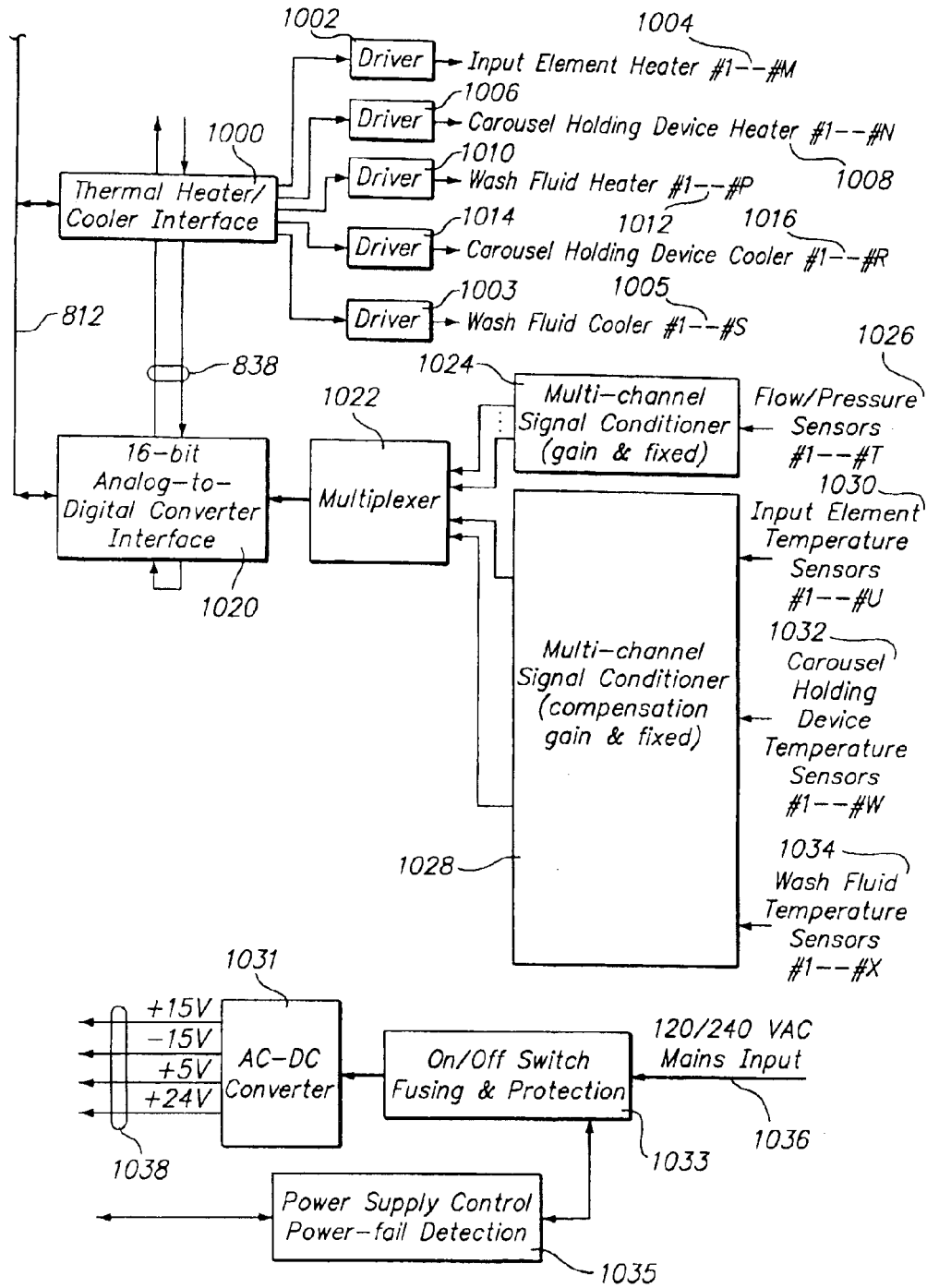
FIG. 17 is a diagrammatic sketch continuation of FIG. 14 illustrating thermal heater/cooler interface, analog-to-digital converter interface and power supply.

The Input Element and portions of the Carousel, as well as the various washing fluids, are held at particular temperatures prescribed by the apparatus' protocols. Temperature control is maintained by thermal heat transfer provided by electric heater/cooler devices controlled through the Thermal Heater/Cooler Interface 1000, (FIG. 17). This interface drives one or more heater devices (1004, 1008, 1012) from drivers 1002, 1006, 1010 respectively. This interface also drives one or more cooling devices 1016, 1005 from drivers 1014, 1003 respectively. Interface 1000 communicates with the Main Microprocessor via bus 812. Software, written in processor-specific assembly language or, preferably, in C/C++ executing in the Main Microprocessor monitors the process temperature and modulates the flow of applied heat energy to maintain the prescribed temperature.

The apparatus incorporates an Analog-to-Digital Converter Interface (FIG. 17) 1020 to monitor the outputs of various analog sensors. Some of these sensors monitor fluid or gas pressures. Others are used to monitor temperature at various locations in the apparatus as part of the temperature control process. The signals from one or more pressure sensors 1026 are conditioned by circuit block 1024 in order to amplify and noise-filter the signals. Signals from one of more temperature sensors 1030, 1032, 1034 are conditioned by circuit block 1028 to cold-junction compensate thermocouples, and amplify and noise-filter the signals. The conditioned signals are input to AID converter 1020 via multiplexer 1022. The A/D converter, with resolution of at least 16-bits, converts the analog signal into digital form for use by the Main Microprocessor 800. These sensor signal levels are used by the process software to control the apparatus.

An alternative to the above-described Main Microprocessor is a commercially available x486 or Pentium class single-board personal computer with standard I/O interfaces and the following attributes: 32-bit processor with a clock speed of at least 200 MHz, at least 128 megabytes of random access memory at least 1 gigabyte disk mass storage, at least 10 megabit/sec Ethernet LAN interface, running a suitable operating system, either Windows NT 4.0 or Linux (or successors thereof). This single board personal computer must be complemented with other function-specific I/O interfaces in order to adapt it to the present apparatus.

Conditioned power needed by the apparatus is supplied by a central power supply, which converts the AC mains power to regulated DC power (FIG. 17). Input power is supplied from the AC mains via lines 1036. The power supply contains a manually or electrically controlled AC mains on/off control switch 1033 with suitable protective fusing in the case of overload or short circuit faults. The power supply contains circuitry 1035 to monitor the condition and quality of the AC mains-supplied power for the purpose of detecting voltage reductions, drop-outs, surges and sags. These conditions are indicated to the Main Microprocessor so that it can take corrective actions with respect to the operation of the apparatus of the invention. Converter 1031 produces the various DC power levels need by the apparatus. In this design, the voltages are commonly +5V, +/−15V and +24V, although other voltages may be produced as needed. Conversion from AC to DC may be made by any means but an auto-ranging input, low-dissipation, high-efficiency switching converter is most common. The auto-ranging input stage of the AC-DC converter 1031 accommodates a wide-range AC input from 90–275 VAC, 40–400 Hz.

To summarize, System Architecture 1 provides a high degree of control system integration. In this architecture, a single main microprocessor provides centralized control of all of the apparatus' functions. It is aided by an auxiliary microprocessor, which performs only diagnostic functions. This architecture directs the activity of the apparatus through various on-chip and off-chip peripheral interfaces to such elements as front-panel displays and controls, to electro-magnetic motors and actuators, to fluid and pneumatic pumps and valves, to temperature and pressure sensors, and to thermal heaters and coolers. These peripheral interfaces are connected to the main microprocessor via an expanded address/data/control bus. Control software executes in the main microprocessor under supervision of a real-time executive or operating system.

Control System Architecture 2

The design concept of System Architecture 2 (FIGS. 8–13) is the distribution of control to dedicated, subsystem-specific, microprocessor-based controller modules: one for over-all system coordination, diagnostics and communication (both intra-apparatus and external communication); one for temperature control; one for fluid and pneumatic actuator control; and one for electromechanical motion control. Each such module performs all the control for a particular aspect (e.g., temperature or motion control) of the present apparatus. Conditioned power is supplied to each of these modules from a system power supply module. Embedded control software executes in each microprocessor module under supervision of a real-time executive.

System Architecture 2 (FIG. 8) comprises multiple control modules interconnected by a multi-channel shared bus (526, 530, 704, 705, 706). The bus makes available to every module the following resources: common system control signals and JTAG scan-bus (lines 526), intra-apparatus data communications network (lines 530), isolated AC power (lines 704) and regulated DC power (lines 706). The bus originates at, and is supervised by, the Central System Controller described below. The modules that connect to the shared bus are: Central System Controller 500, System Power Supply 700, Temperature Controller 550, Fluidic and Pneumatic Controller 600, and Motion/motor Controller 650.

The Central System Controller 500 (FIG. 9) provides (1) high-level supervision and coordination of the other subsystem controller modules, (2) communication with the user via the displays and user controls, and (3) communication between the apparatus and external systems and among the subsystem modules. It comprises a 16 or 32-bit general purpose microprocessor 502 equipped with suitable data RAM 504, program ROM 506, and boot ROM 508. The microprocessor group (502, 504, 506, 508) connects to six communication interfaces and controllers via a local address and data bus structure 532. User controls and displays 520, connect to the digital I/O interface 512, via lines 522. These displays and controls permit the operator to interact with the apparatus. Diagnostic controller 514, with associated RS-232 serial data communications port 524, supports apparatus self-test. This controller also connects to external test systems that direct more rigorous subsystem testing and diagnosis. The IEEE Standard 1149-compatible JTAG scan-bus controller 516 interfaces to all subsystem modules via lines 526. This controller supports subsystem diagnostics and a means for the Central System Controller to download the program memories of other subsystem modules. The intra-station network interface 510 coordinates and controls communication among the subsystems via lines 530. This internal network 530 provides a means to exchange status and control information between subsystem modules and the Central System Controller. The external serial I/O interface 518 provides high-speed 10/100-BaseT Ethernet data communication between the apparatus and external systems via network media 528. Bar code Reader Interface 534 and associated sensor 536, read the bar code label on each support housing as it is moved from the Input Element to the carousel Holding Device. This bar code is used to track the identity and location of the support housing as it is processed by the apparatus described herein. The Central System Controller is governed by an embedded real-time operating system and custom application-specific software to control the tasks, operation actions and methods described herein. The embedded operating system software may be written in processor-specific assembly language or preferably, in C/C++. The custom application-specific software may be written in C/C++.

The Power Supply module 700 (FIG. 10) contains circuitry to condition the input power and convert it from AC to DC for use by the system. Input power is supplied from the AC mains via lines 702. The Power Supply module contains a manually or electrically controlled AC mains on/off control switch and suitable protective fusing in the case of overload or short circuit faults 708. This module contains a transformer 712 (or other means) to produce AC isolated from the mains for use in powering AC motor and heater loads isolated from the mains. Isolated AC power is distributed to other subsystems via lines 704. In addition, the Power Supply module contains circuitry 710 to monitor the condition and quality of the AC mains-supplied power for detecting voltage reductions, drop-outs, surges and sags. These conditions are indicated to the Central System Controller module, via line 705, so that it can take corrective actions with respect to the operation of the apparatus of the invention. Finally, this module contains circuitry 714 to convert the AC input power to DC power at the various voltages and current levels needed by the system's other circuitry. This conversion may be made by an auto-ranging input, low-dissipation, high-efficiency AC-DC converter (or other means) 714. The auto-ranging input stage of the AC-DC converter accommodates AC inputs from 90–275 VAC, 40–400 Hz. The output of this module supplies the entire apparatus of the invention with power and feeds regulated +5V, +/–15V and +24V DC, for example, to the other subsystem modules via the shared bus 706.

The Temperature Controller 550 (FIG. 11) provides semi-autonomous control of all the heating and cooling functions of the apparatus of the invention. It is based on a general purpose 16-bit microcomputer 554, which incorporates suitable amounts of data RAM memory 555 and non-volatile program ROM memory (e.g., down-loadable, re-programmable FLASH memory technology) 556, a serial data communications interface 558 and a multiple lines (bits) of general-purpose digital I/O 560. Minimum RAM memory size is typically 8K bytes and program ROM size is typically 64K bytes. The microcontroller also interfaces with the system's IEEE Standard 1149-compatible JTAG scan-bus 526. These elements are all part of typical state-of-the-art single-chip microcomputers. The embedded serial data communications interface 558 connects the Temperature Controller to the other intra-apparatus modules via the intra-station network 530. Temperature measurement and controller status information is communicated via this network 530 to the Central System Controller in order to coordinate the actions of the apparatus of the invention. The general-purpose digital I/O interface 560 controls the heating and cooling elements of the apparatus through zero-crossing detector and driver circuits 570, 572, 574, 576, and 584. Zero crossing detector 570 in conjunction with drivers 572, 574, 576 (or solid-state relay equivalents) control and modulate the application of isolated AC power 704 to the Input Element heating elements #1---#M, 578; to the Carousel Holding Device heating elements #1---#N, 580; and to the Wash Fluid heating elements #1---#P, 582. Such drivers are commonly pulse-width modulated and incorporate zero-crossing trigger circuits to minimize the generation of electromagnetic interference caused by load switching. Other drivers 584 control and modulate the application of electric power to the Carousel Holding Device cooling elements #1 . . . #R, 586; and to the Wash Fluid cooling elements #1---S, 588. The general-purpose digital I/O interface also connects various types of temperature sensors to the controller via an analog-to-digital converter (A/D) 562 and its associated sensor multiplexer 564. Temperature sensors associated with each temperature control loop may be thermocouple (TC) or resistance temperature detector (RTD) types. The electrical signals from these sensors are conditioned (cold-junction compensated, normalized, amplified and low-pass filtered) by analog circuitry 566. There are three groups of temperature sensor signals: Input Element sensors #1---#U, 568; Carousel Holding Device sensors #1---W, 567; and Wash Fluid sensors #1---#X, 569. Each of these signals is selected in sequence for input into the A/D converter 562 by multiplexer 564. The A/D converter quantizes the time-continuous analog signal into discrete digital form for use by the Temperature Controller's embedded software control algorithm. This control algorithm linearizes the sensor signals and controls the corresponding heating/cooling elements through a conventional proportional-integral-differential (PID) type algorithm. The actions of the Temperature Controller are governed by an embedded real-time executive and application-specific software to control the tasks, operation actions and methods described herein. The embedded executive software may be written in processor-specific assembly language or preferably, in C/C++. The application-specific software may be written in C/C++.

The Fluidic and Pneumatic Controller 600 (FIG. 12) is a module that provides semi-autonomous control of all the fluid pumps, valves & circuits and all pneumatic (air or nitrogen gas) valves & circuits of the apparatus or the invention. This controller is based on a general purpose 8 or 16-bit microcomputer 602, which incorporates suitable amounts of data RAM 603 and non-volatile program ROM (e.g., down-loadable, re-programmable FLASH memory technology) 604, a serial data communications interface 606, multiple lines (bits) of general-purpose digital I/O 608, and an on-chip analog multiplexer and 12-bit analog-to-digital converter 620. Minimum RAM size is typically 8K bytes and program ROM size is typically 64K bytes. The microcontroller may also interface with the system's IEEE Standard 1149-compatible JTAG scan-bus 526. These elements are all part of typical state-of-the-art single-chip microcomputers. The embedded serial data communications interface connects the Fluidic and Pneumatic Controller to the other intra-apparatus modules via the intra-station network 530. Fluid flow measurement and controller status information is communicated via this network 530 to the Central System Controller in order to coordinate the actions of the apparatus of the invention. The general-purpose digital I/O interface 608 controls the fluid and pneumatic valves of the apparatus through driver circuits 614. These high-current and/or high-voltage drivers provide on/off and proportional control of fluid and gas flows by operating electro-fluidic or electro-pneumatic valves 618, 622, 624, 626, 628, 630. Specifically these valves comprise: valves #1 and #2 of the First Fluid Dispensing station, 618 622 respectively; valves #1 and #2 of the Second Fluid Dispensing station, 624 626 respectively; and mixing valves #1 and #2, 628 630 respectively. The on-chip analog multiplexer and A/D converter 620 connects to various types of pressure or flow sensors #1---#T, 616 associated with each control loop. The electrical signals from these sensors are conditioned (i.e., compensated, normalized, amplified and filtered) by analog circuitry 612. Each of these signals is selected in sequence by the multiplexer and A/D converter 620. The A/D converter quantizes the time-continuous analog signals into discrete digital form for use by the controller's embedded software. The actions of the Fluidic and Pneumatic Controller are governed by an embedded real-time executive and application-specific software to control the tasks, operation actions and methods described herein. The embedded executive software may be written in processor-specific assembly language or preferably, in C/C++. The application-specific software may be written in C/C++.

The Motion/Motor Controller 650 (FIG. 13) provides semi-autonomous control of all the motion functions of the present apparatus including pneumatic actuators, step- and servomotor controls. It is based on a general purpose 32-bit microcomputer 652, which incorporates suitable amounts of data RAM memory 653 and non-volatile program ROM (e.g., down-loadable, re-programmable FLASH memory technology) 654, a serial data communications interface 658 and a multiple lines (bits) of general-purpose digital I/O 656. Minimum data RAM memory size is 8 Kbytes and program ROM memory size is typically 64 Kbytes. The microcontroller interfaces with the system's IEEE Standard 1149-compatible JTAG scan-bus 526. These elements are all part of typical state-of-the-art single-chip microcomputers. The embedded serial data communications interface connects the Motion/Motor Controller to the other intra-apparatus modules via the intra-station network 530. Motion commands and position status information is communicated via this network 530 to the Central System Controller in order to coordinate the actions of the apparatus of the invention. The general-purpose digital I/O interface 656 controls the twelve pneumatic actuators (e.g., cylinders) stepping and servomotors of the apparatus through an array of driver circuits. Such drivers may be on/off types or, more commonly, pulse-width modulated and incorporate zero-crossing trigger circuits to minimize the generation of electromagnetic interference caused by load switching. The general-purpose digital I/O interface also connects various types of position, direction and angle encoders and force, velocity and acceleration sensors to the controller. The electrical signals from these sensors are conditioned (i.e., compensated, normalized, amplified and filtered) by decoder circuitry. These signals are used by the controller's application-specific software to govern the position, velocity and acceleration of the dynamic parts of the apparatus through conventional proportional-integral-differential (PID) type algorithms. Specifically, the Input Element Elevator motor 664 is controlled through step/servo driver 662 and position/velocity decoder 668; the Input Element Loader motor 672 is controlled through step/servo driver 670 and position/velocity decoder 674; the Carousel Holding Device motor 678 is controlled through step/servo driver 676 and position/velocity decoder 680; the Lid Rotator motor 684 is controlled through step/servo driver 682 and position/velocity decoder 686; the Lid Lifter motor 690 is controlled through step/servo driver 688 and position/velocity decoder 692; the Lid Translator motor 696 is controlled through step/servo driver 694 and position/velocity decoder 698; the Spin Dryer Loader motor 752 is controlled through step/servo driver 750 and position/velocity decoder 754; the Spin Dryer Rotor motor 758 is controlled through step/servo driver 756 and position/velocity decoder 760; the First Fluid Dispensing Station nozzle elevation motor 764 is controlled through step/servo driver 762 and position/velocity decoder 766; the Second Fluid Dispensing Station nozzle elevation motor 770 is controlled through step/servo driver 768 and position/velocity decoder 772; the Output Element Elevator motor 776 is controlled through step/servo driver 774 and position/velocity decoder 778; the Output Element Loader motor 782 is controlled through step/servo driver 780 and position/velocity decoder 784. The actions of the Motion/motor Controller are governed by an embedded real-time executive and application-specific software to control the tasks, operation actions and methods described herein. The embedded executive software may be written in processor-specific assembly language or preferably, in C/C++. The application-specific software may be written in C/C++.

To summarize, System Architecture 2 is a modular design in which control of the apparatus is distributed among several control modules. Each controller module is designed for a particular control function (i.e., temperature, fluid, gas, motion, etc). Architectural modularity leads to an optimized functional design. System Architecture 2 provides (1) overall supervision of apparatus activity by a Central System Control module, (2) a collection of specialized subsystem controllers which provide semi-autonomous behavior within their scope of control, (3) multi-channel intra-apparatus communication network which permits communication and coordination among the various subsystem controllers, (4) a modular, easily extensible architecture.

Control System Architecture 3

Figure 5:
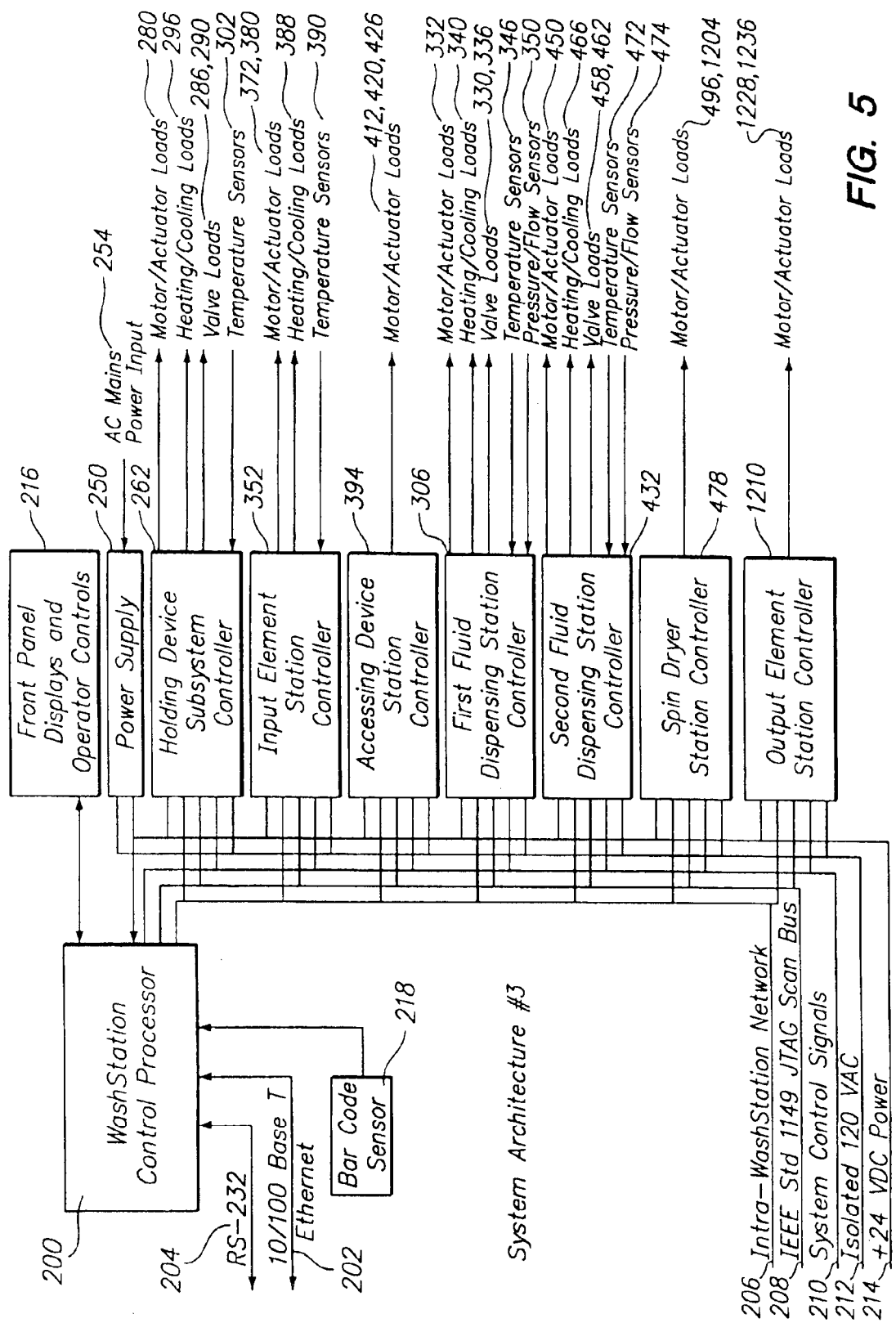
FIG. 5 is a diagrammatic sketch of one embodiment of a control system architecture for an apparatus in accordance with the present invention.
Figure 6:
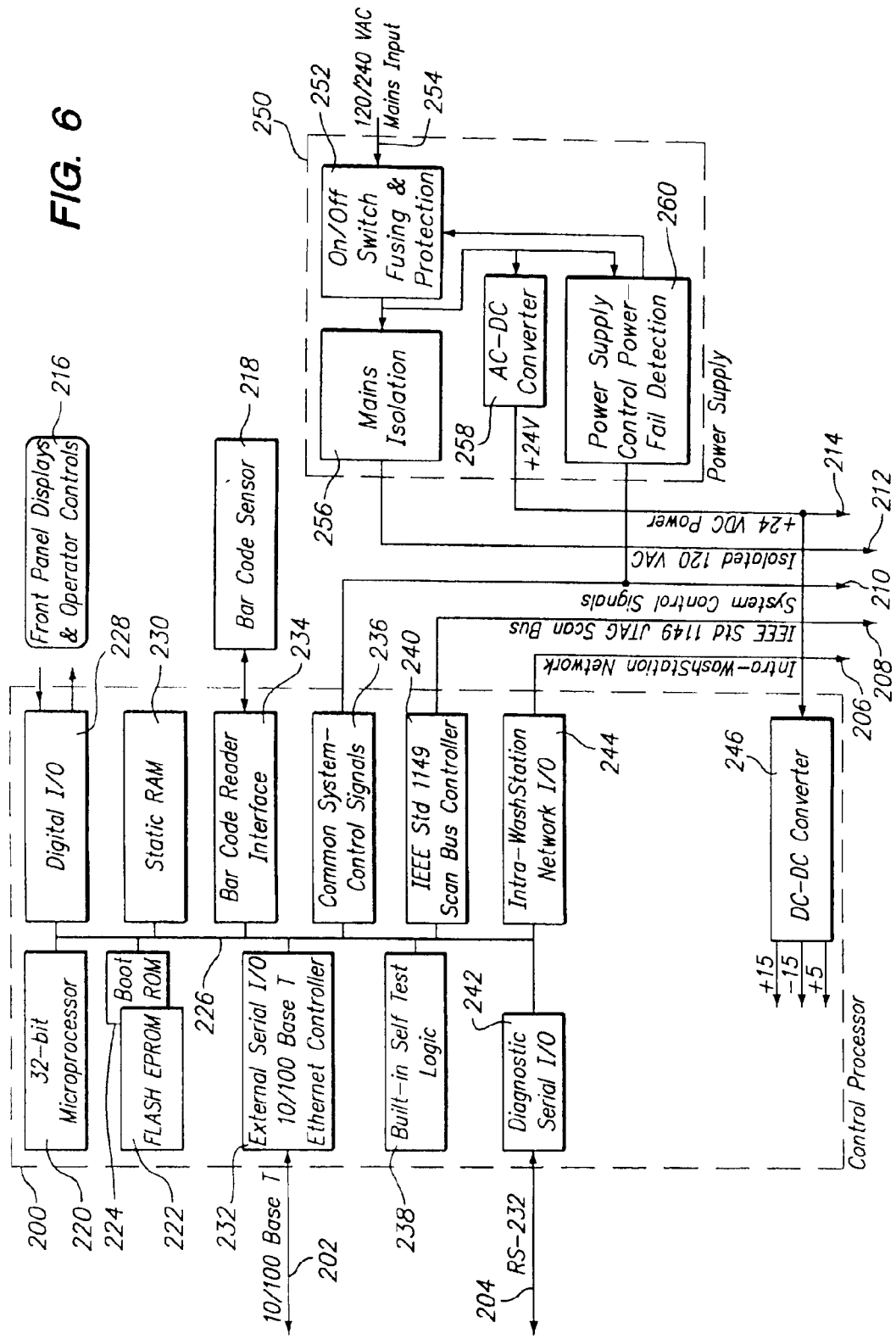
FIG. 6 is a diagrammatic sketch of a control processor module and a power supply module for the control system architecture of FIG. 5.
Figure 7A:
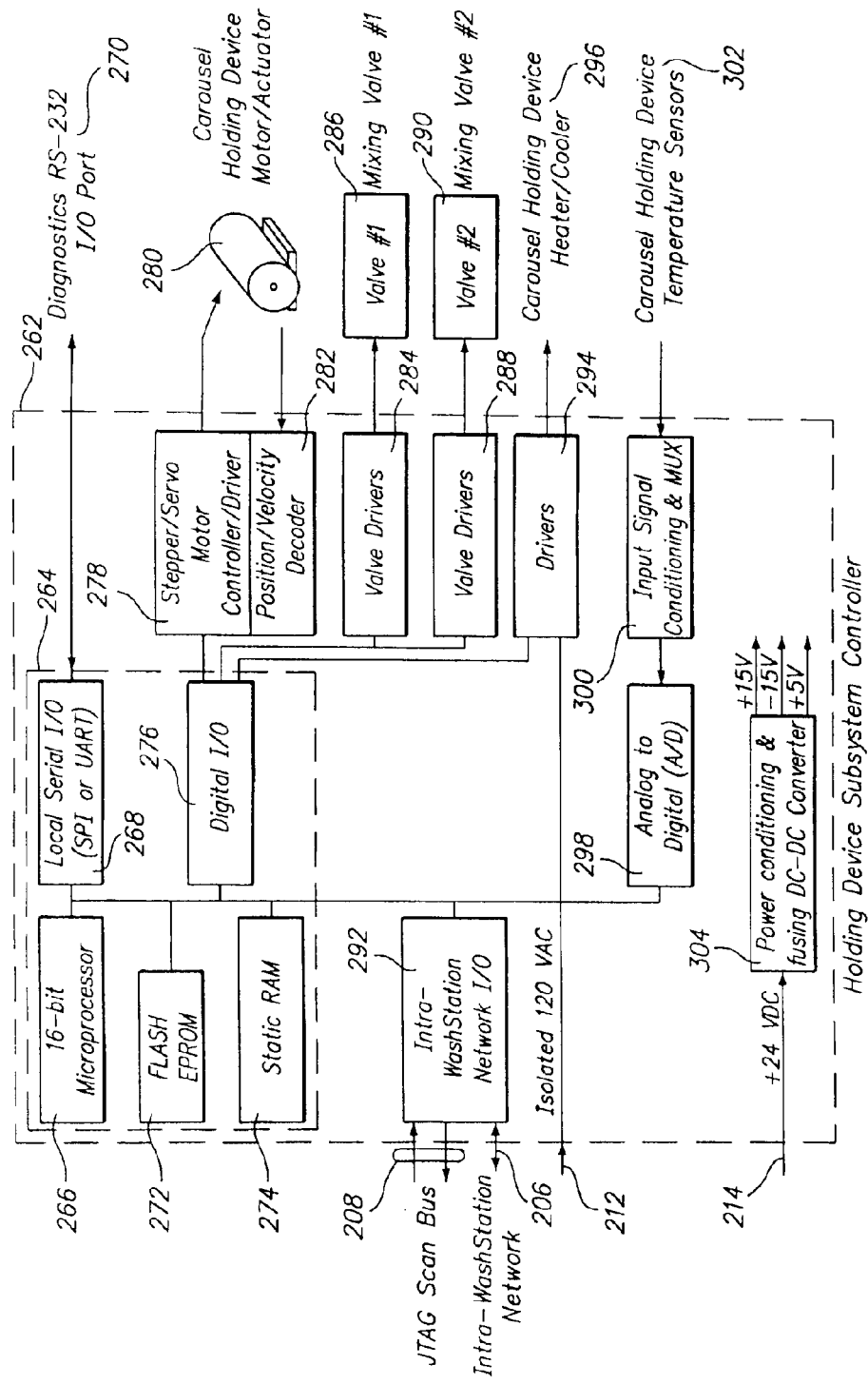
FIG. 7A is a diagrammatic sketch of a holding device subsystem controller module for the control system architecture of FIG. 5.
Figure 7B:
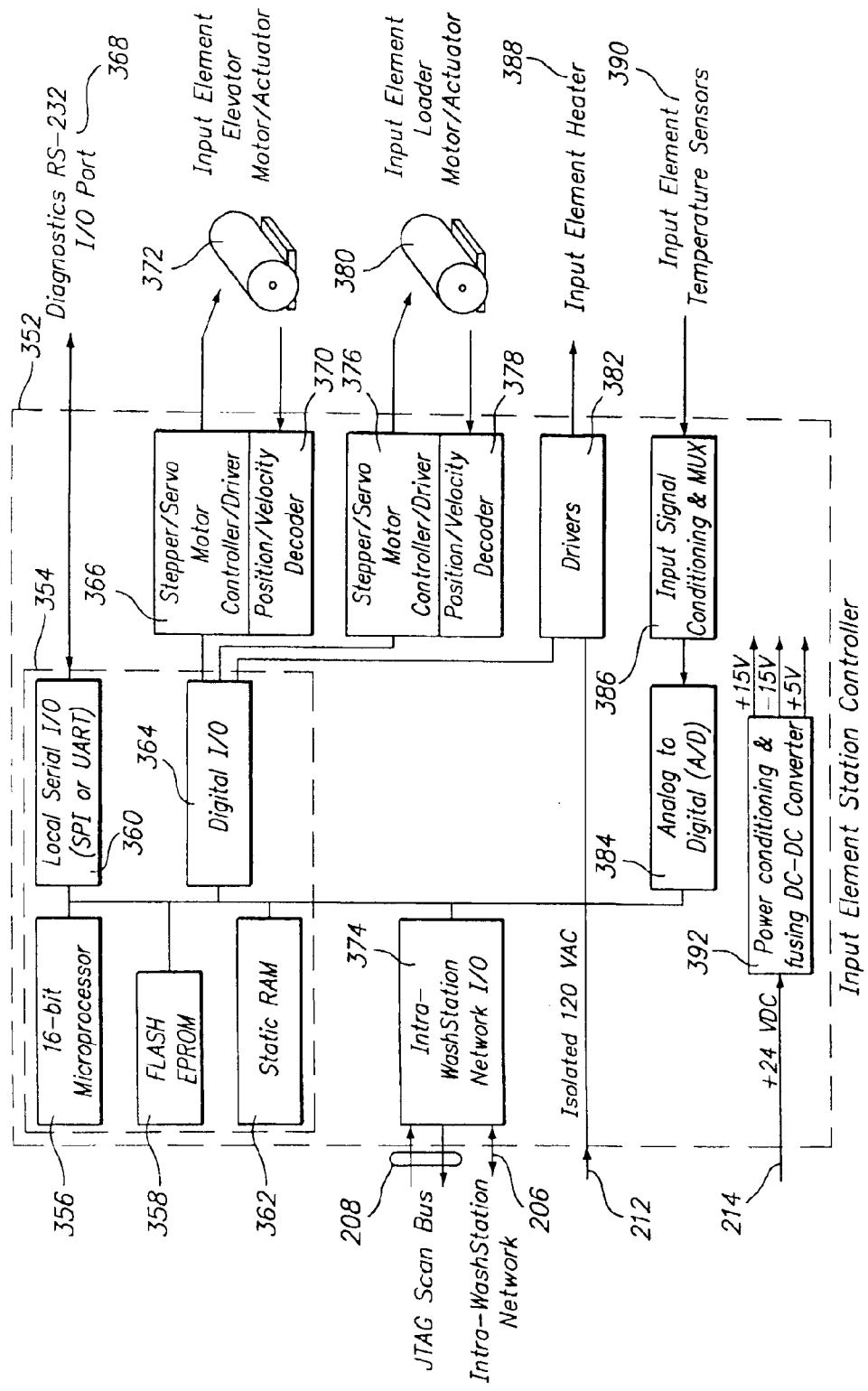
FIG. 7B is a diagrammatic sketch of an input element station controller module for the control system architecture of FIG. 5.
Figure 7C:
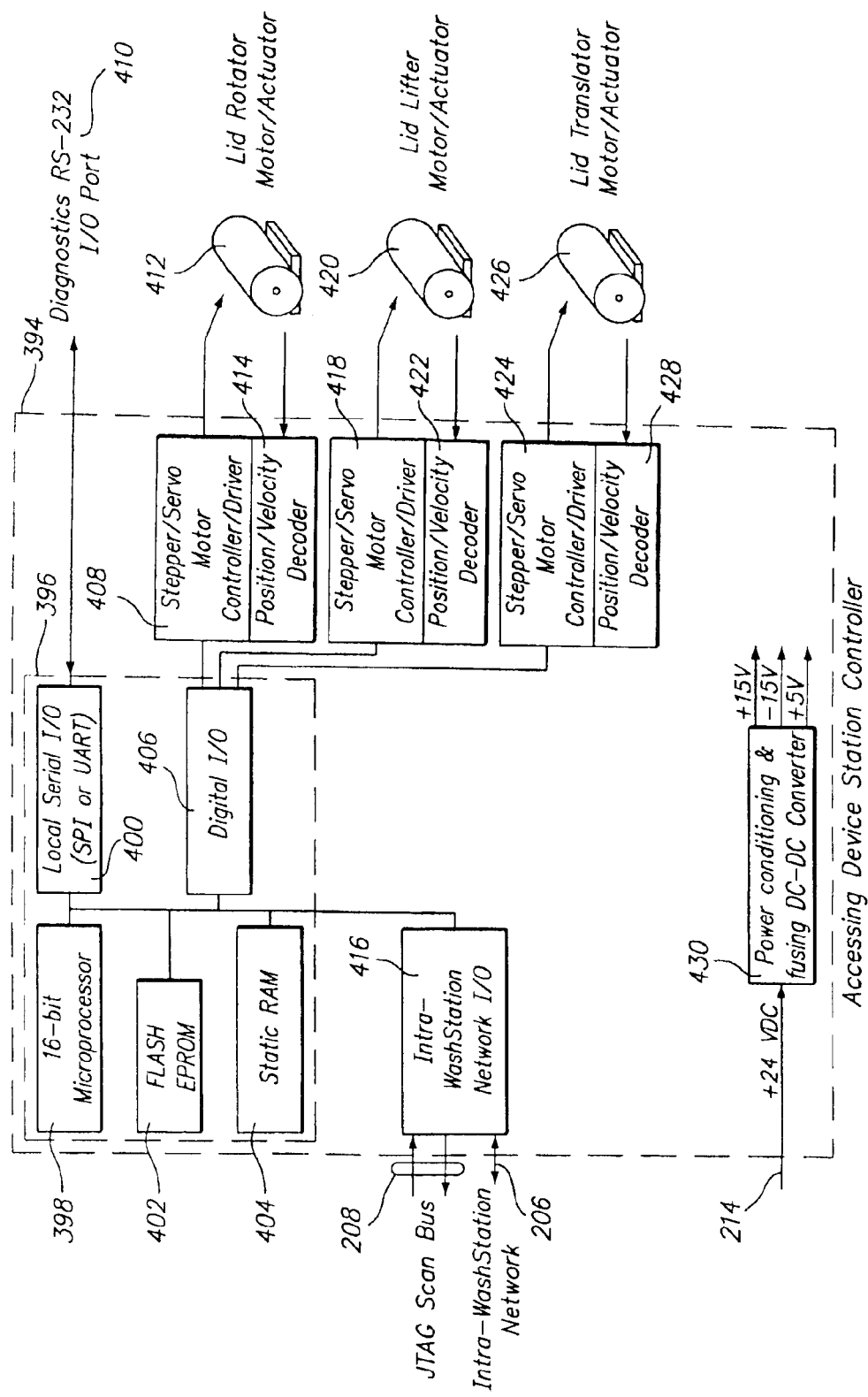
FIG. 7C is a diagrammatic sketch of an accessing device station controller module for the control system architecture of FIG. 5.
Figure 7D:
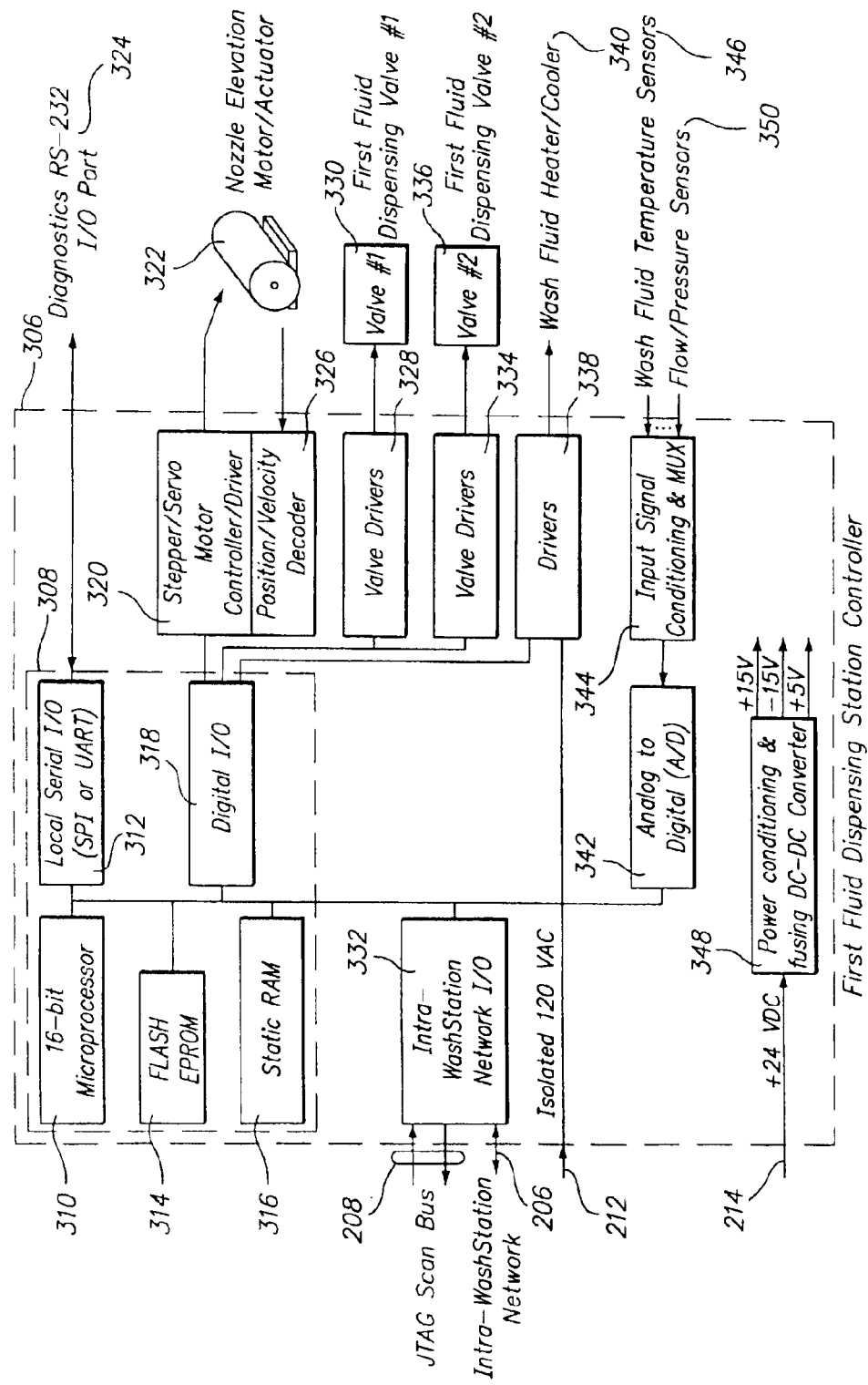
FIG. 7D is a diagrammatic sketch of a first fluid dispensing station controller module for the control system architecture of FIG. 5.
Figure 7E:
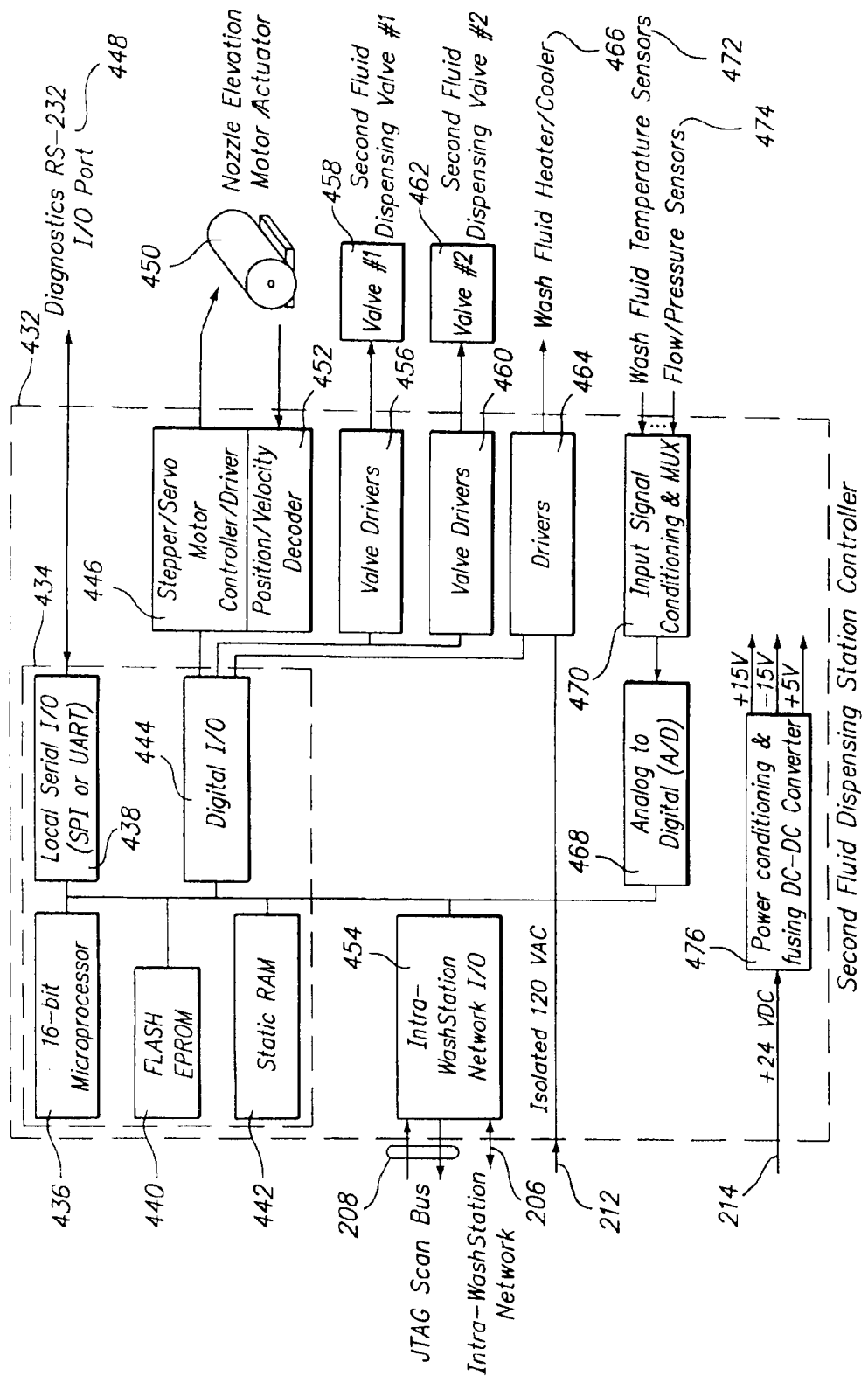
FIG. 7E is a diagrammatic sketch of a second fluid dispensing station controller module for the control system architecture of FIG. 5.
Figure 7F:
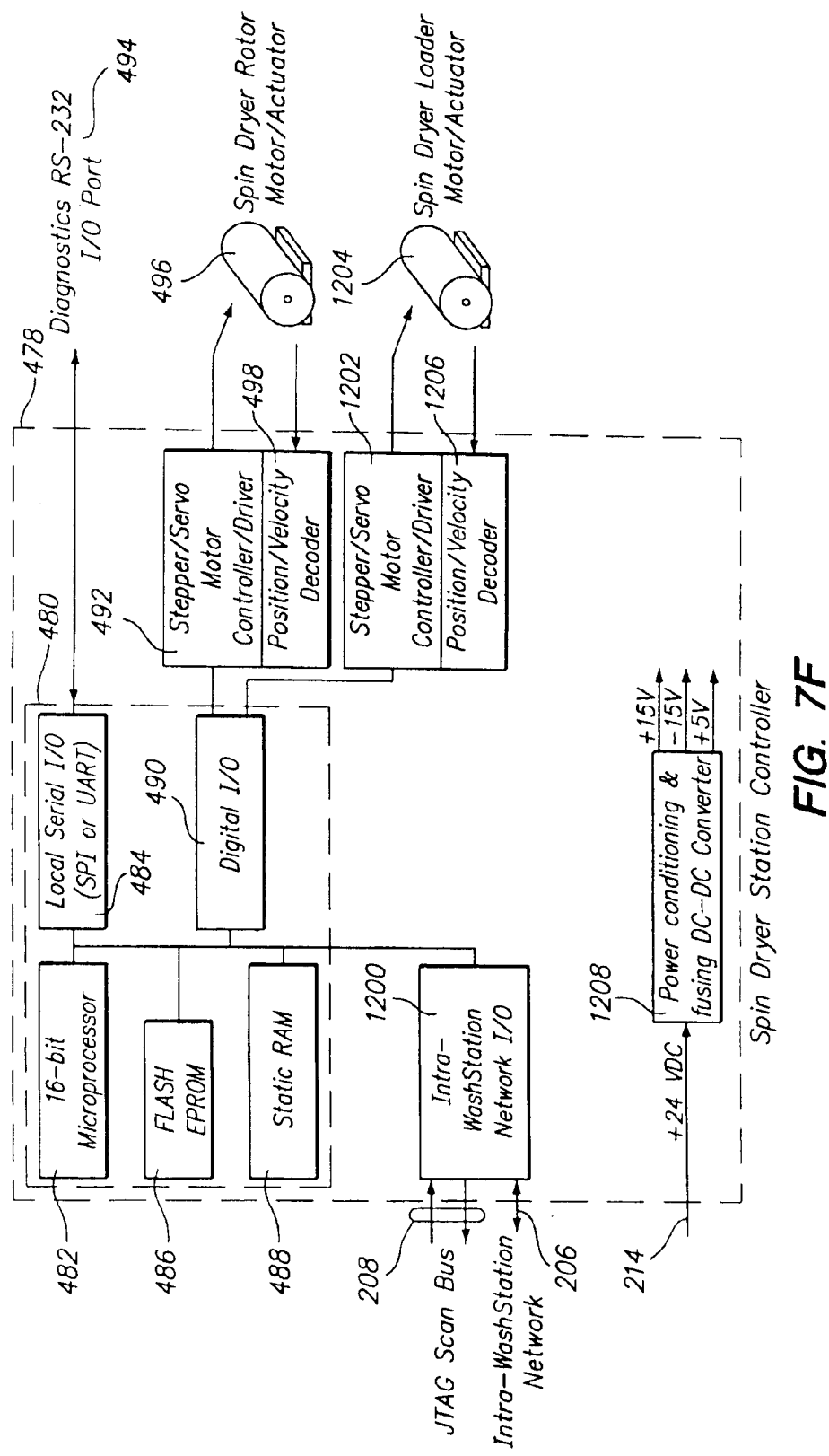
FIG. 7F is a diagrammatic sketch of a spin dryer station controller module for the control system architecture of FIG. 5.
Figure 7G:
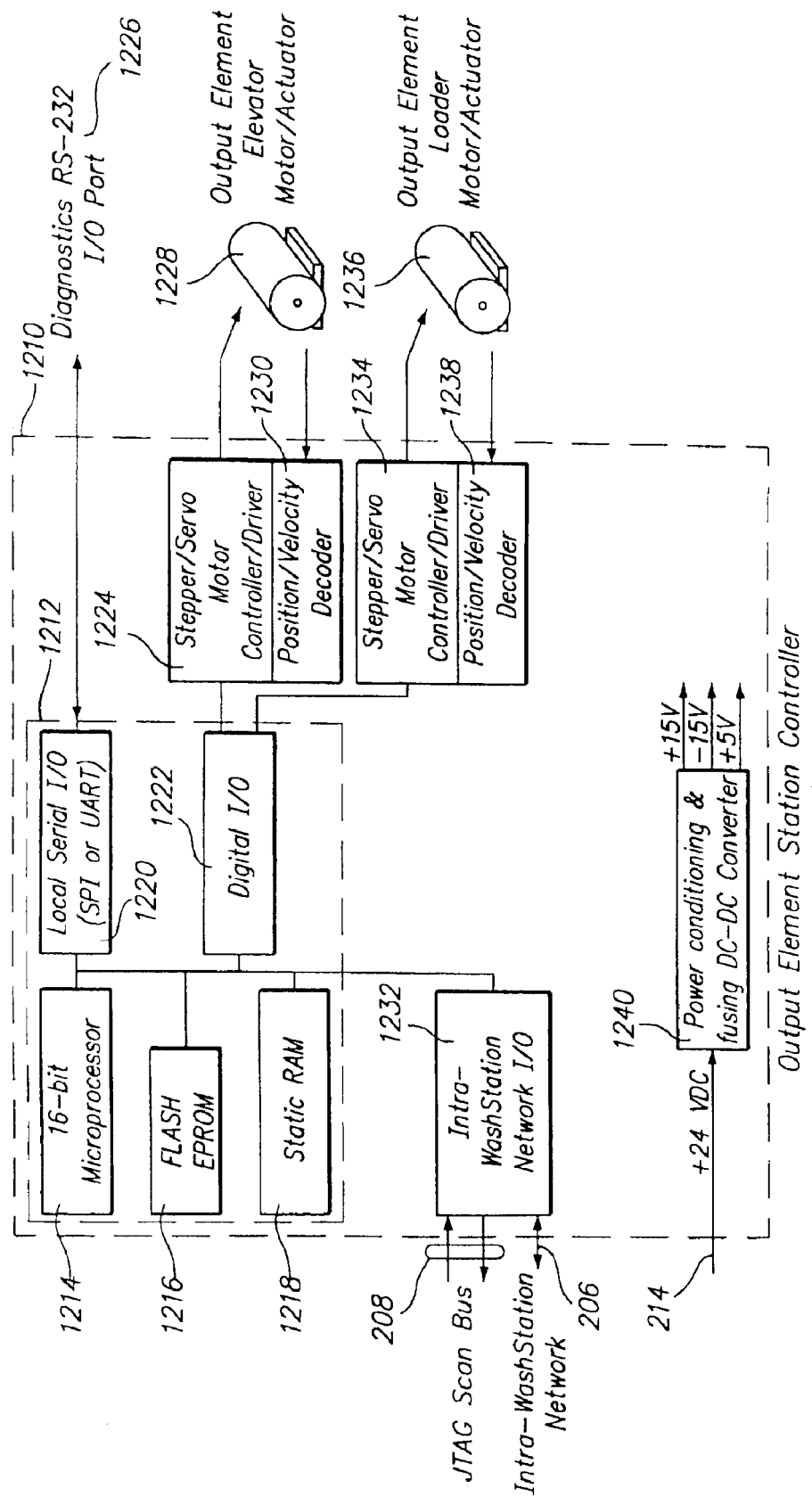
FIG. 7G is a diagrammatic sketch of an output element station controller module for the control system architecture of FIG. 5.
Figure 8:
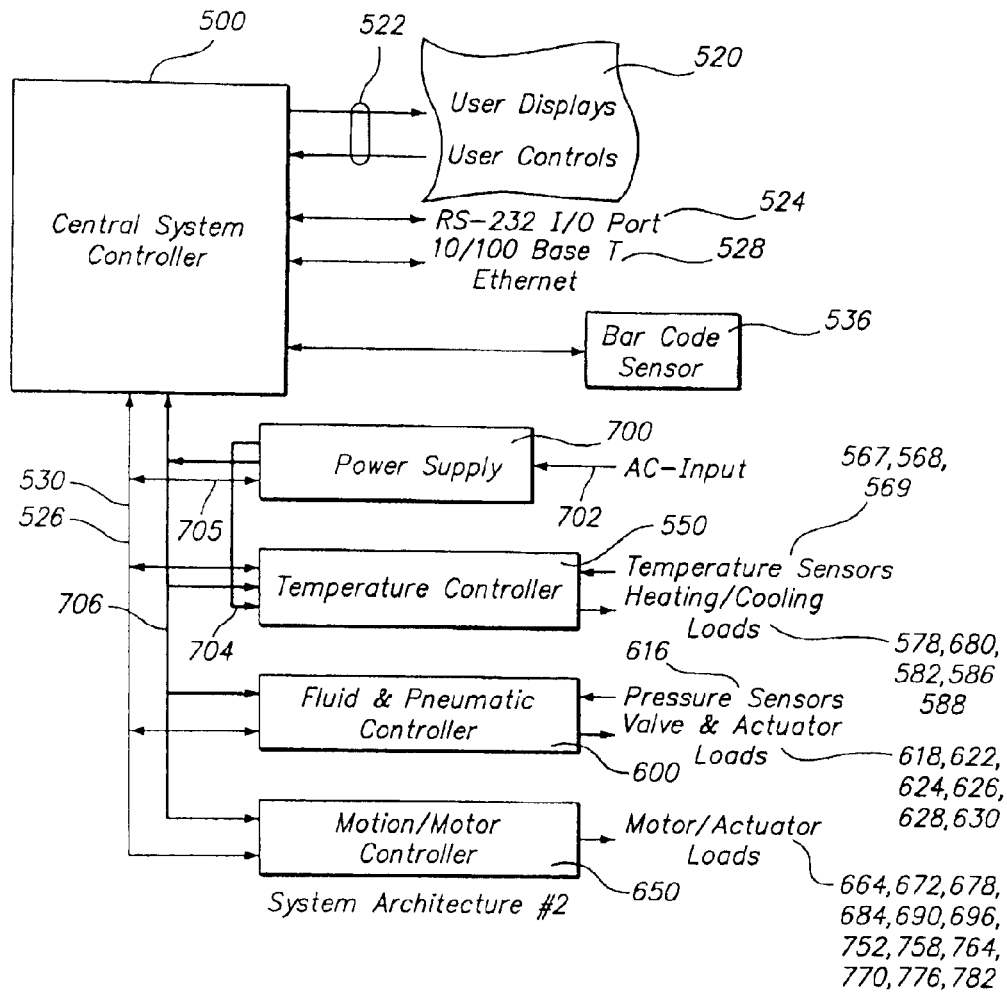
FIG. 8 is a diagrammatic sketch of another embodiment of a control system architecture for an apparatus in accordance with the present invention.
Figure 9:
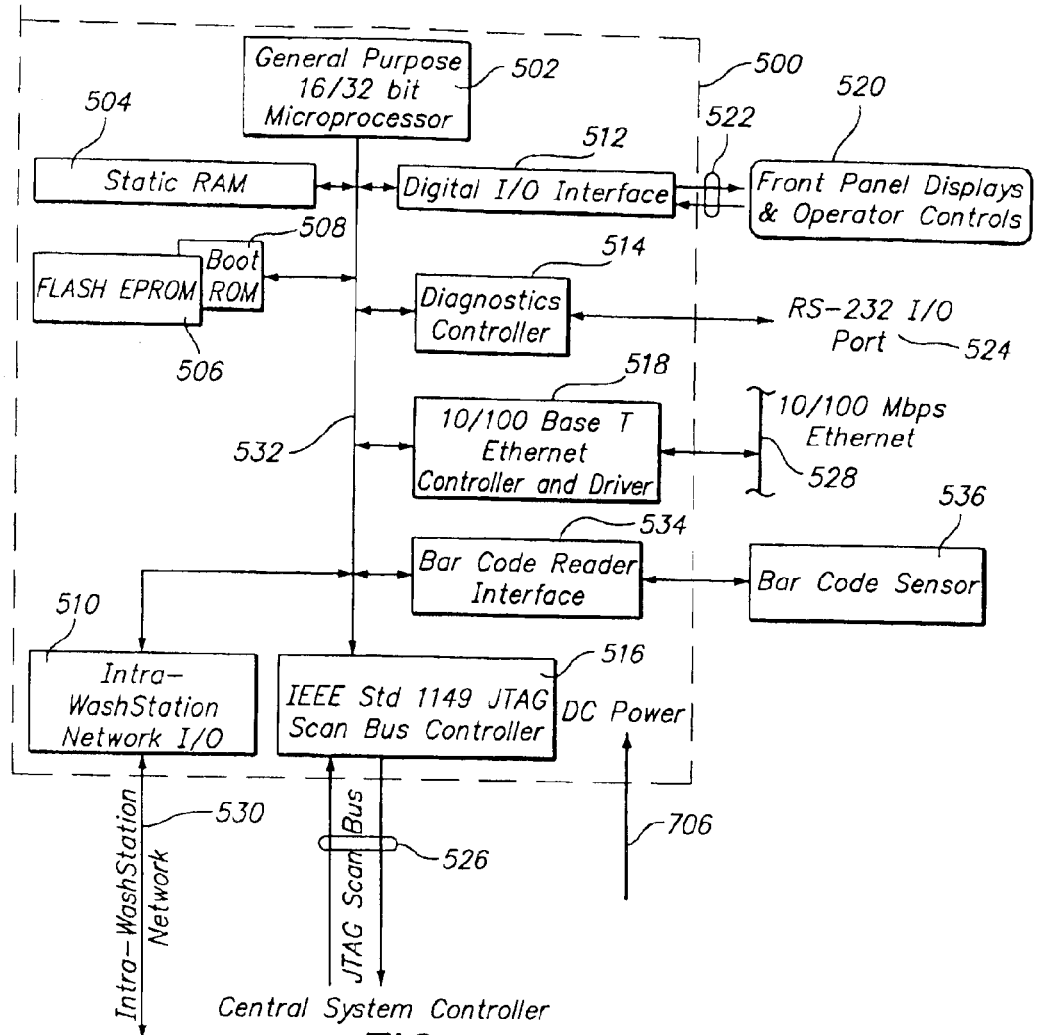
FIG. 9 is a diagrammatic sketch of a central-system controller module for the control system architecture of FIG. 8.
Figure 10:
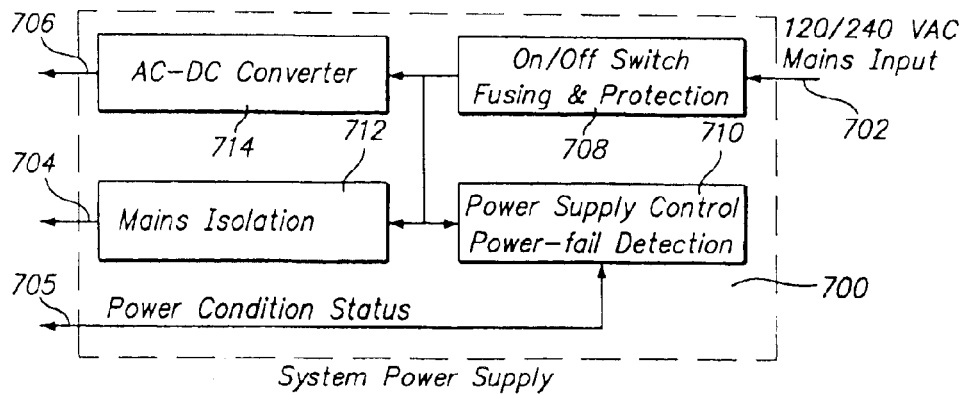
FIG. 10 is a diagrammatic sketch of a power conditioner module for the control system architecture of FIG. 8.
Figure 11:
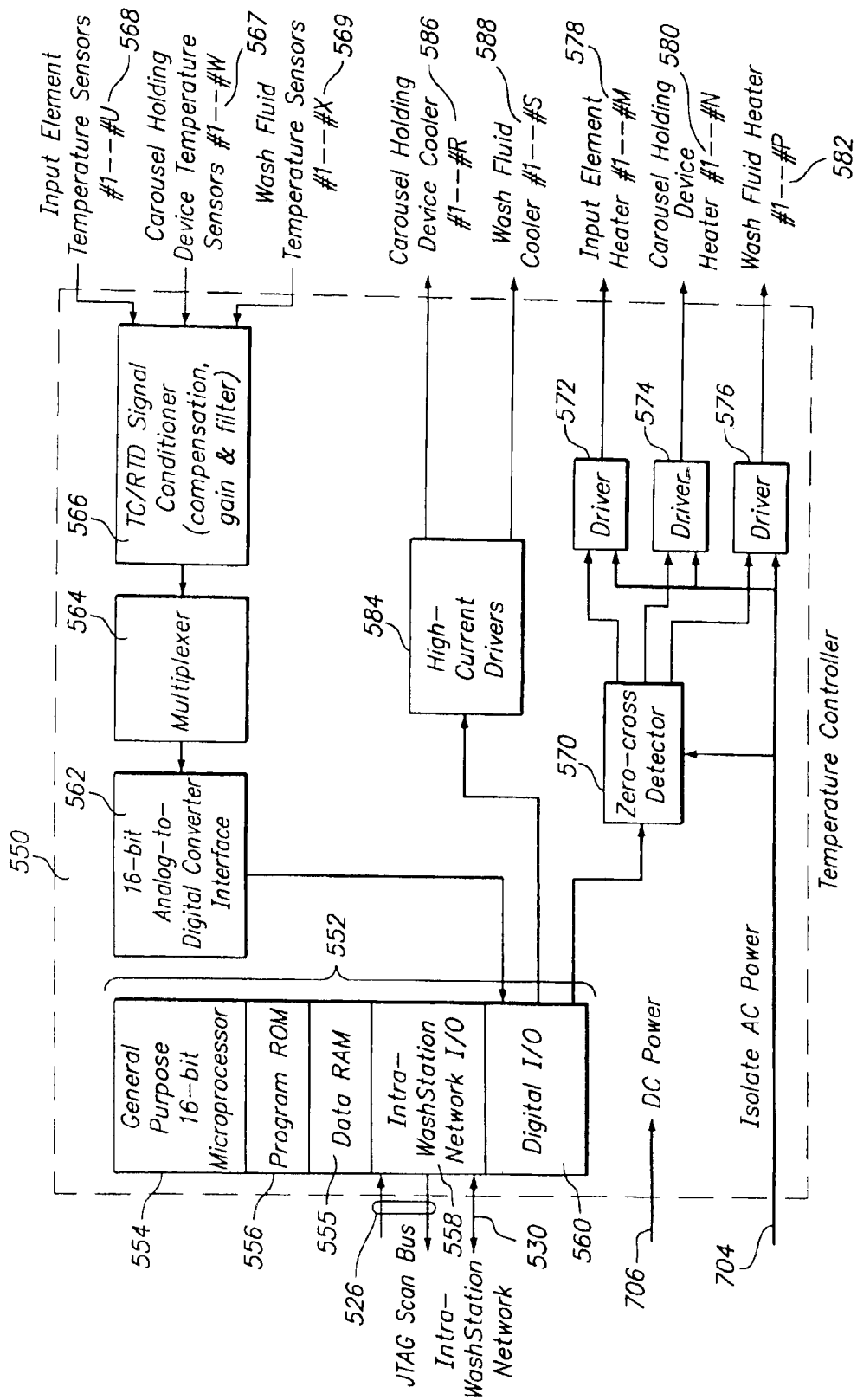
FIG. 11 is a diagrammatic sketch of a temperature controller module for the control system architecture of FIG. 8.
Figure 12:
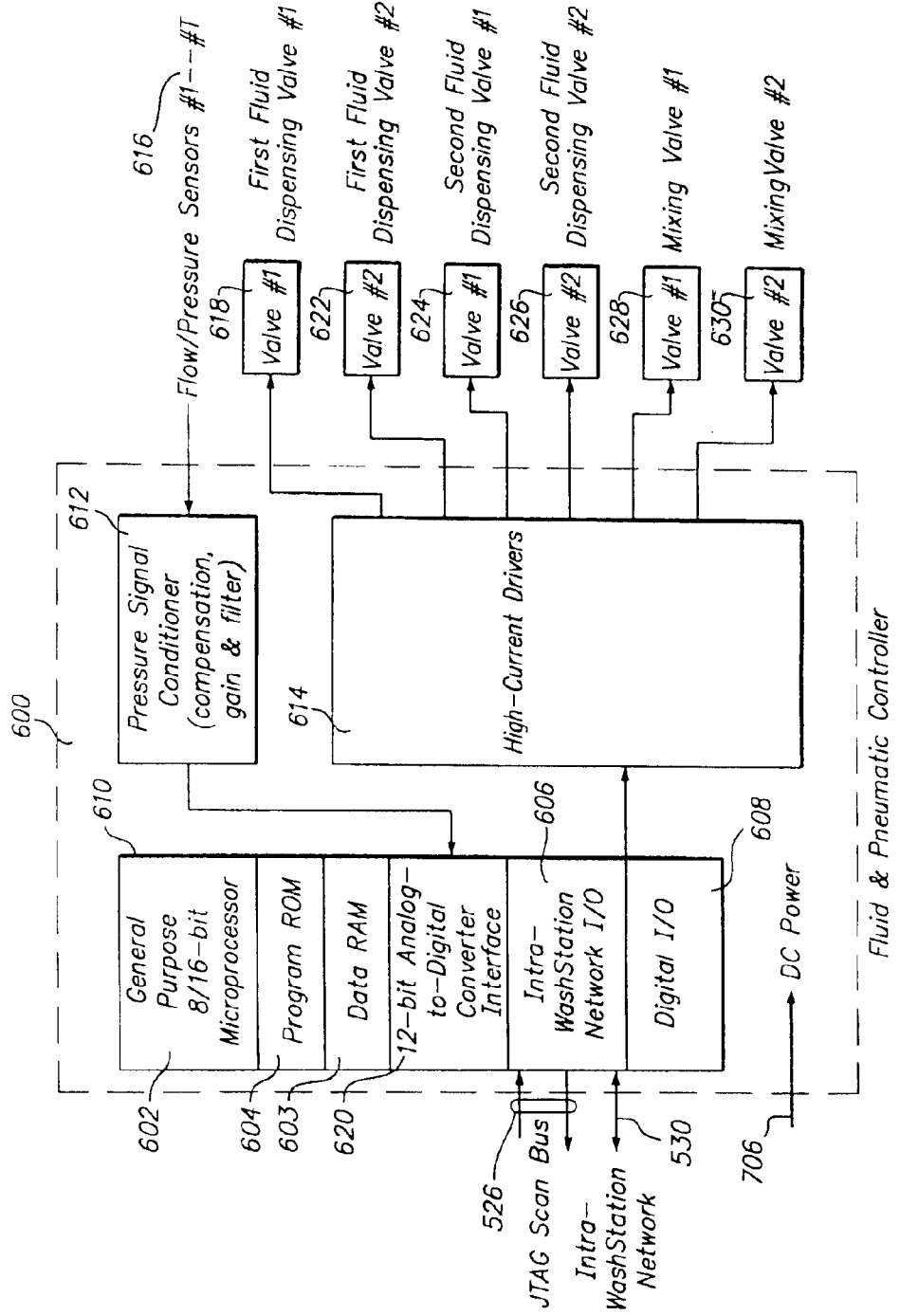
FIG. 12 is a diagrammatic sketch of a fluids and gas controller module for the control system architecture of FIG. 8.
Figure 13A:
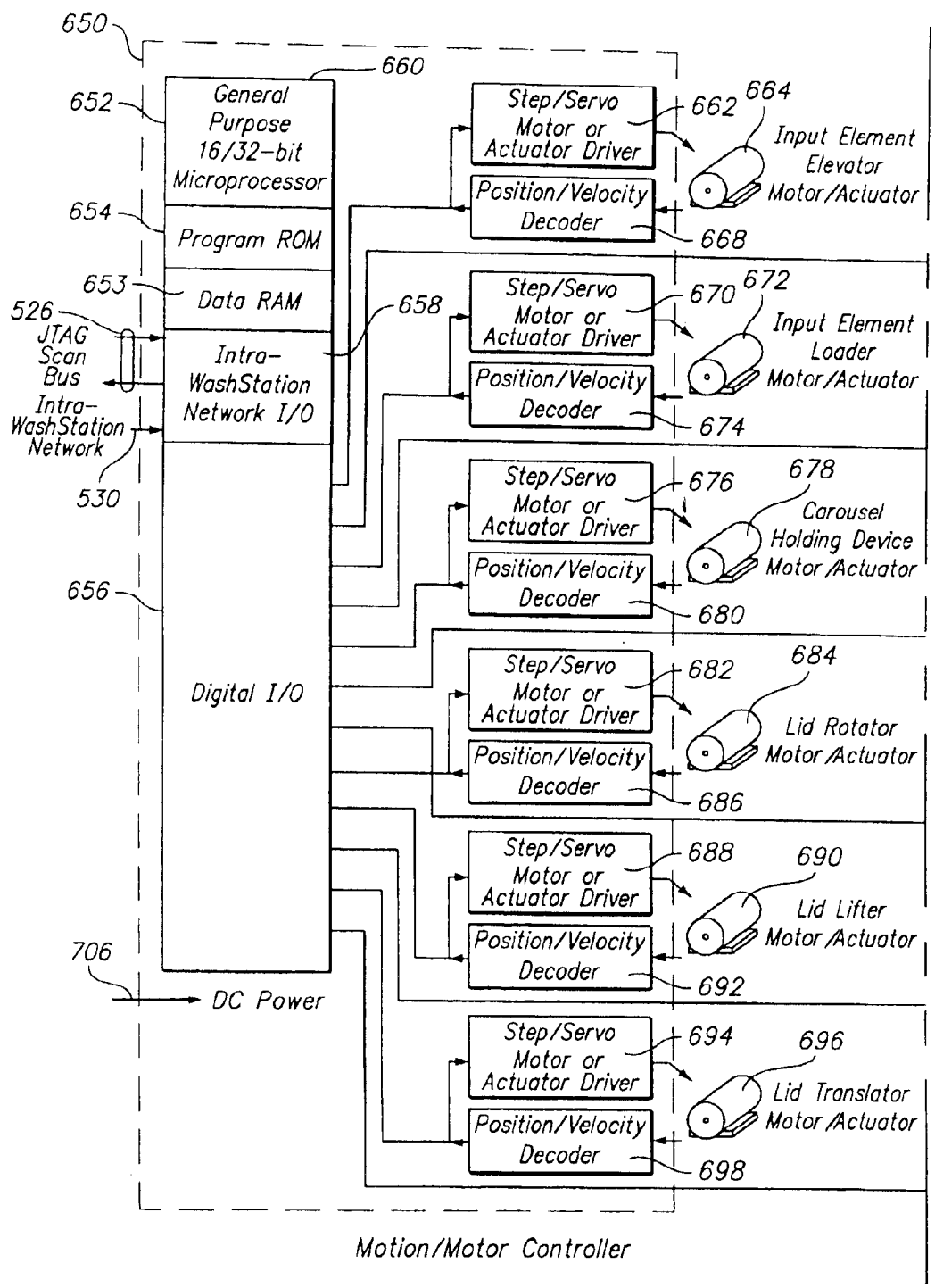
FIG. 13 is a diagrammatic sketch of a motion controller module for the control system architecture of FIG. 8.
Figures 13, 13B:
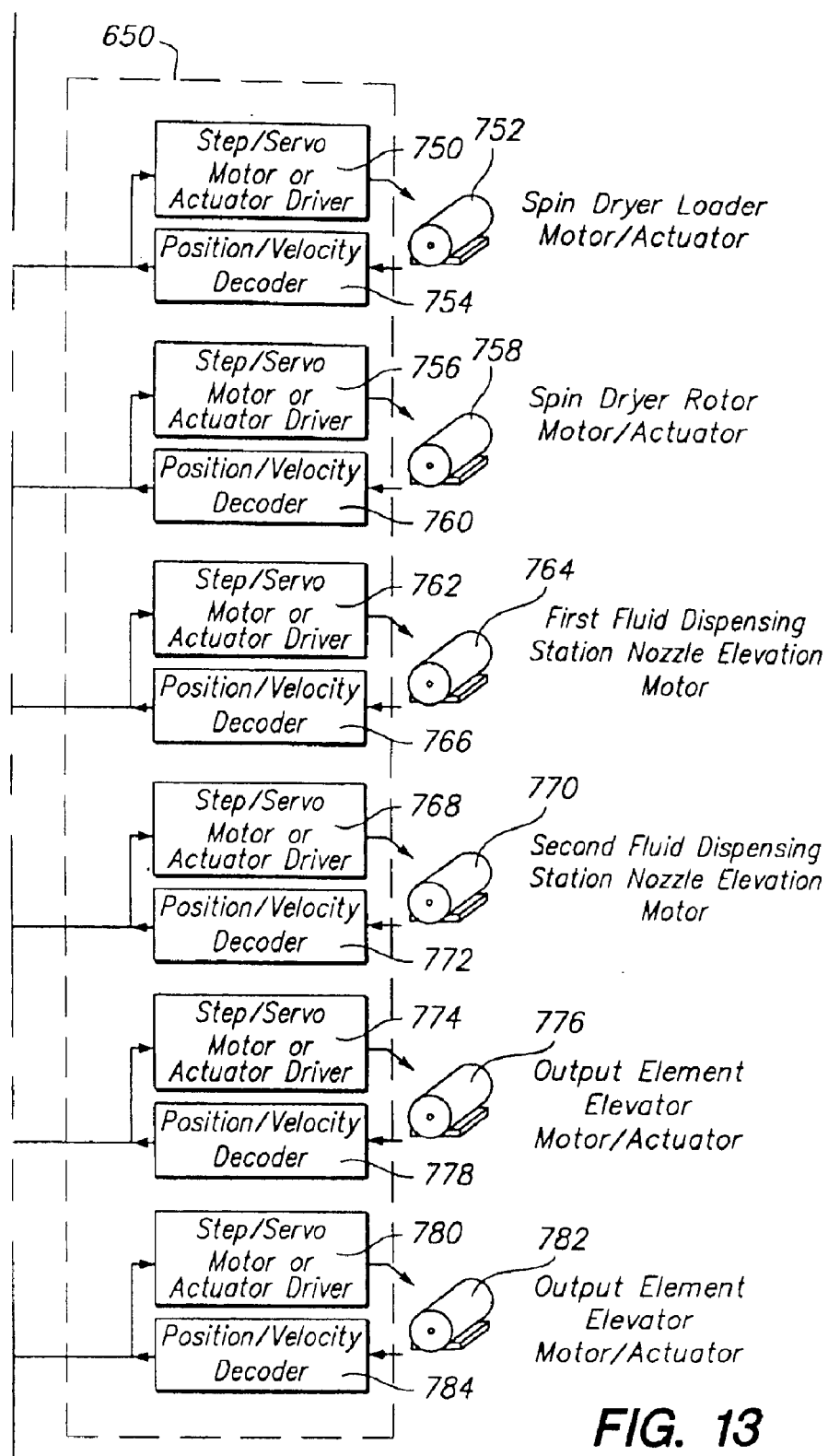

The design concept of System Architecture 3 (FIG. 5) is the distribution of control to dedicated, subsystem-specific, microprocessor-based controller modules. Each of these is capable of low-level semi-autonomous control of a particular part of the apparatus mechanism. The controller modules which comprise System Architecture 3 are: a Control Processor 200 for overall control (FIG. 6), one for controlling all aspects of the Carousel Holding Device 262 (FIG. 7A), one for controlling all aspects of the Input Element Station 352 (FIG. 7B), one for controlling all aspects of the Accessing Device Station 394 (FIG. 7C), one for controlling all aspects of the First Fluid Dispensing Station 306 (FIG. 7D), one for controlling all aspects of the Second Fluid Dispensing Station 432 (FIG. 7E), one for controlling all aspects of the Spin Dryer Station 478 (FIG. 7F), and one for controlling all aspects of the Output Element Station 1210 (FIG. 7G). Each controller module performs all of the control (motion, temperature, fluid flow, etc) for a particular station of the present apparatus. Communication among these controller modules occurs by means of a multi-channel shared bus (FIG. 5). The bus originates at, and is supervised by, Control Processor 200. The bus makes the following resources available to every module: isolated 120V AC power (line 212), common system control signals (line 210), IEEE Standard 1149-compatible JTAG scan-bus signals (line 208), intra-apparatus data communications network (line 206), and regulated 24V DC power (line 214). Conditioned power is supplied to each of these modules from a system power supply module 250 (FIG. 6). The actions of each station controller are governed by embedded real-time executive and application-specific software to control the required tasks and functions. The embedded executive software may be written in processor-specific assembly language or preferably, in C/C++. The custom application-specific software may be written in C/C++.

Each of the controller modules of this architecture is described below. The Control Processor 200 (FIG. 6) is based on a 32-bit microprocessor 220, which incorporates non-volatile program storage memory 222 (e.g., based on re-programmable FLASH memory technology) to contain the embedded control software, non-volatile boot-memory 224 to aid in system start-up and initialization, static data RAM 230, and various digital I/O interfaces. Digital I/O interface 228 communicates with front-panel displays and operator controls 216 to permit operators to observe and interact with the apparatus. Interface 234 and sensor 218 support reading of the bar codes associated with each support housing. Digital interface 236 generates the various common system control signals needed by each module of the system. Common system control signals, for example, system clock, reset, interrupts, and the like, are conveyed to the other modules via multi-signal line 210. Digital communication among the modules of the system for the purposes of synchronizing action and communicating process data and status are supported by digital interface 244 via line 206. IEEE Standard 1149-compatible JTAG scan-bus communication among the modules of the system for the purposes of diagnostic testing and fault detection is supervised by scan-bus controller and interface 240 via lines 208. Elements 238 and 242 contain circuitry to support Control Processor self-testing for diagnostic purposes. They include an RS-232 digital I/O interface 204, which serves as a diagnostic port to external test systems. Such systems may be used to control and test the apparatus in ways that are more rigorous than, and differ from, normal operation. Communication with external systems occurs through the 10/100 BaseT Ethernet interface 232 via lines 202. This interface provides 10 Mbps or 100 Mbps serial data communication to supervisory computer systems or data servers. The circuitry of the Control Processor is powered from the DC-DC converter, 246. The actions of the Control Processor are governed by embedded real-time executive and application-specific software to control the tasks, operation actions and methods described herein.

The Power Supply module 250 (FIG. 6) contains circuitry to condition the mains input power supplied by line 254 and convert it from AC to DC for use by all of the system. This module comprises a manually or electrically controlled AC mains on/off control switch 252 with suitable protective fusing in the case of overload or short circuit faults and a transformer (or other means) 256 to produce AC power isolated from the mains for use in powering isolated AC motor and heater loads. Isolated AC power is distributed to every module of the system via line 212. In addition, the Power Supply 250 contains circuitry 260 to monitor the condition and quality of the AC mains supplied power, thus, indicating voltage reductions, drop-outs, surges and sags to the Control Processor 200 so that it can take corrective actions with respect to the operation of the system. Finally, this module contains circuitry to convert the AC input power to DC power at the various voltages and current levels needed by the system's other circuitry. This conversion is made by an auto-ranging input, low dissipation high-efficiency AC-DC converter 258 (or other means). The auto-ranging input stage of the AC-DC converter accommodates AC inputs from 90–275VAC, 40–400 Hz. The output of this converter supplies regulated 24V DC to the Control Processor and all other subsystem modules via line 214.

The Carousel Holding Device station 262 (FIG. 7A) consists of a DC-DC converter 304, a processor group 264, communication interfaces to the other controller modules of the system 292, and a variety of digital and analog I/O interfaces 298, 276 to the station's motor, valve actuators, and sensors.

The power conditioning circuitry 304 converts the +24V DC supplied by the shared bus 214 to the voltages and current levels needed by the subsystem's electronics, sensors and actuators, typically +5V, +15V and −15V. This conversion is best made by a low-dissipation, high-efficiency DC-DC converter or other acceptable means.

The processor group 264 contains a general purpose microprocessor 266 with the following specifications: 16-bit word length, clock speed of at least 30 MHz, at least 64 Kbytes of non-volatile FLASH program memory 272, at least 16 Kbytes of data RAM 274, an expanded address/data bus interface, SPI and UART serial interface 268 to diagnostic RS-232 I/O port 270, and a multi-bit digital I/O interface 276. The processor group 264 interfaces to the unique mix of sensors and actuators through a set of digital and analog interfaces. General purpose analog-to-digital converter 298 with signal conditioning and multiplexer circuitry 300 interface to the station's Carousel Holding Device temperature sensors 302. This AID converter has a minimum resolution of 12 bits. Sensor signals are conditioned and multiplexed by circuitry 300 to amplify and filter them. The processor's digital I/O interface 276 controls various motors, valves and heating/cooling devices associated with the station. Specifically, this interface controls: (1) the station's carousel transport motor 280 through stepper/servo motor driver 278 and position/velocity decoder 282 in order to position the support housings at the desired processing station; (2) fluid mixing valve #1 286 through driver 284 and fluid mixing valve #2 290 through driver 288 to agitate the fluids associated with this station; and (3) holding device heater and cooling elements 296 through driver 294 to warm and cool the holding devices loaded onto the carousel. Driver 294 incorporates zero-crossing detection circuitry to minimize the generation of EMI. The heater/cooler elements are energized by isolated AC power supplied by bus 212. Communication with other station controllers is supported through the intra-wash station network I/O interface 292 via buses 206 and 208. This controller module is also linked to the Control Processor 200 through an IEEE Std-1149 JTAG scan bus 208. The JTAG bus supports down loading of software into the station control processor and it supports hardware diagnostics. Processor 266 is governed by embedded real-time executive and application-specific software to control the required tasks and operation activity of the station.

The Input Element station controller 352 (FIG. 7B) consists of a DC-DC converter 392, a processor group 354, communication interfaces to the other controller modules of the system 374, and a variety of digital and analog I/O interfaces 364, 384 to the station's motor, heaters, and sensors.

The power conditioning circuitry 392 converts the +24V DC supplied by the shared bus 214 to the voltages and current levels needed by the subsystem's electronics, sensors and actuators, typically +5V, +15V and −15V. This conversion is best made by a low-dissipation, high-efficiency DC-DC converter or other acceptable means.

The processor group 354 contains a general purpose microprocessor 356 with the following specifications: 16-bit word length, clock speed of at least 30 MHz, at least 64 Kbytes of non-volatile FLASH program memory 358, at least 16 Kbytes of data RAM 362, an expanded address/data bus interface, SPI and UART serial interface 360 to diagnostic RS-232 I/O port 368, and a multi-bit digital I/O interface 364. The processor group 354 interfaces to the unique mix of sensors and actuators through a set of digital and analog interfaces. General purpose analog-to-digital converter 384 with signal conditioning and multiplexer circuitry 386 interface to the station's input element temperature sensors 390. This A/D converter has a minimum resolution of 12 bits. Sensor signals are conditioned and multiplexed by circuitry 386 to amplify and filter them. The processor's digital I/O interface 364 controls various motors and heating/cooling devices associated with the station. Specifically, this interface controls: (1) the Input Element elevator motor 372 through stepper/servo motor drivers 366 and position/velocity decoder 370 in order to position the support housings to the plane of the carousel transport mechanism; (2) the Input Element loader motor 380 through stepper/servo motor drivers 376 and position/velocity decoder 378 in order to transfer support housings from the Input Element to the Carousel Holding Device; and (3) Input Element heater elements 388 through driver 382 to warm the support housings contained in the Input Element. Driver 382 incorporates zero-crossing detection circuitry to minimize the generation of EMI. The heater elements are energized by isolated AC power supplied by bus 212. Communication with other station controllers is supported through the intra-wash station network I/O interface 374 via buses 206 and 208. This controller module is also linked to the Control Processor 200 through an IEEE Std-1149 JTAG scan bus 208. The JTAG bus supports down loading of software into the station control processor and it supports hardware diagnostics. Processor 356 is governed by embedded real-time executive and application-specific software to control the required tasks and operation activity of the station.

The Accessing Device station controller 394 (FIG. 7C) consists of a DC-DC converter 430, a processor group 396, communication interfaces to the other controller modules of the system 416, and a variety of digital interfaces 406 to the station's motors.

The power conditioning circuitry 430 converts the +24V DC supplied by the shared bus 214 to the voltages and current levels needed by the subsystem's electronics, sensors and actuators, typically +5V, +15V and −15V. This conversion is best made by a low-dissipation, high-efficiency DC-DC converter or other acceptable means.

The processor group 396 contains a general purpose microprocessor 398 with the following specifications: 16-bit word length, clock speed of at least 30 MHz, at least 64 Kbytes of non-volatile FLASH program memory 402, at least 16 Kbytes of data RAM 404, an expanded address/data bus interface, SPI and UART serial interface 400 to diagnostic RS-232 I/O port 410, and a multi-bit digital I/O interface 406. The processor's digital I/O interface 406 controls various motors associated with the station: (1) the Lid Rotator motor 412 through stepper/servo motor driver 408 and position/velocity decoder 414 in order to rotate the lid of the support housing position in preparation for its removal; (2) the Lid Lifter motor 420 through stepper/servo motor driver 418 and position/velocity decoder 422 in order to pull the lid away from the support housing; and (3) the Lid Translator motor 426 through stepper/servo motor driver 424 and position/velocity decoder 428 in order to discard the lid of the support housing. Communication with other station controllers is supported through the intra-wash station network I/O interface 416 via buses 206 and 208. This controller module is also linked to the Control Processor 200 through an IEEE Std-1149 JTAG scan bus 208. The JTAG bus supports down loading of software into the station control processor and it supports hardware diagnostics. Processor 398 is governed by embedded real-time executive and application-specific software to control the required tasks and operation activity of the station.

System Architecture 3 incorporates two separate fluid dispensing stations 306 (FIG. 7D) and 432 (FIG. 7E) which are capable of low-level semi-autonomous control of their respective stations. These two stations differ in the type of fluids they process, but are identical in all other electromechanical aspects. Only the First Fluid Dispensing station will be described in detail. Component designations refer to the First Fluid Dispensing station, with those for the Second Fluid Dispensing station indicated in brackets [. . . ]. The First Fluid Dispensing station consists of a DC-DC converter 348 [476], a processor group 308 [434], communication interfaces to the other controller modules of the system 332 [454], and a variety of digital and analog I/O interfaces 318, 342 [444,468] to the station's motor, valves, heaters, coolers, and sensors.

The power conditioning circuitry 348 [476] converts the +24V DC supplied by the shared bus 214 to the voltages and current levels needed by the subsystem's electronics, sensors and actuators, typically +5V, +15V and −15V. This conversion is best made by a low-dissipation, high-efficiency DC-DC converter or other acceptable means.

The processor group 308 [434] contains a general purpose microprocessor 310 [436] with the following specifications: 16-bit word length, clock speed of at least 30 MHz, at least 64 Kbytes of non-volatile FLASH program memory 314 [440], at least 16 Kbytes of data RAM 316 [442], an expanded address/data bus interface, SPI and UART serial interface 312 [438] to diagnostic RS-232 I/O port 324 [448], and a multi-bit digital I/O interface 318 [444].

The processor group 308 [434] interfaces to the unique mix of sensors and actuators through a set of digital and analog interfaces. General purpose analog-to-digital converter 342 [468] with signal conditioning and multiplexer circuitry 344 [470] interface to the station's wash fluid temperature sensors 346 [472] and pressure/flow sensors 350 [474]. This A/D converter has a minimum resolution of 12 bits. Sensor signals are conditioned and multiplexed by circuitry 344 [470] to amplify and filter them. The processor's digital I/O interface 318 [444] controls various motors, valves and heating/cooling devices associated with the station. Specifically, this interface controls: (1) the station's nozzle elevation motor 322 [450] through stepper/servo motor driver 320 [446] and position/velocity decoder 326 [452] in order to raise and lower the fluid dispensing nozzles to access the interior volume of the support housing; (2) fluid dispensing valve #1 330 [458] through driver 328 [456] and fluid dispensing valve #2 336 [462] through driver 334 [460] to dispense and aspirate fluid associated with this station; and (3) fluid heater and cooling elements 340 [466] through driver 338 [464] to warm and cool the process fluids consumed by the station. Driver 338 [464] incorporates zero-crossing detection circuitry to minimize the generation of EMI. The heater /cooler elements are energized by isolated AC power supplied by bus 212. Communication with other station controllers is supported through the intra-wash station network I/O interface 332 [454] via buses 206 and 208. This controller module is also linked to the Control Processor 200 through an IEEE Std-1149 JTAG scan bus 208. The JTAG bus supports down loading of software into the station control processor and it supports hardware diagnostics. Processor 310 [436] is governed by embedded real-time executive and application-specific software to control the required tasks and operation activity of the station.

The Spin Dryer station controller 478 (FIG. 7F) consists of a DC-DC converter 1208, a processor group 480, communication interfaces to the other controller modules of the system 1200, and a variety of digital interfaces 490 to the station's motors.

The power conditioning circuitry 1208 converts the +24V DC supplied by the shared bus 214 to the voltages and current levels needed by the subsystem's electronics, sensors and actuators, typically +5V, +15V and −15V. This conversion is best made by a low-dissipation, high-efficiency DC-DC converter or other acceptable means.

The processor group 480 contains a general purpose microprocessor 482 with the following specifications: 16-bit word length, clock speed of at least 30 MHz, at least 64 Kbytes of non-volatile FLASH program memory 486, at least 16 Kbytes of data RAM 488, an expanded address/data bus interface, SPI and UART serial interface 484 to diagnostic RS-232 I/O port 494, and a multi-bit digital I/O interface 490. The processor's digital I/O interface controls various motors associated with the station: (1) the spin dryer rotor motor 496 through stepper/servo motor driver 492 and position/velocity decoder 498 in order to centrifugally dry the support housing; and (2) the spin dryer loader motor 1204 through stepper/servo motor driver 1202 and position/velocity decoder 1206 in order to transfer the support housing between the carousel holding device and spin dryer. Communication with other station controllers is supported through the intra-wash station network I/O interface 1200 via buses 206 and 208. This controller module is also linked to the Control Processor 200 through an IEEE Std-1149 JTAG scan bus 208. The JTAG bus supports down loading of software into the station control processor and it supports hardware diagnostics. Processor 482 is governed by embedded real-time executive and application-specific software to control the required tasks and operation activity of the station.

The Output Element station controller 1210 (FIG. 7G) consists of a DC-DC converter 1240, a processor group 1212, communication interfaces to the other controller modules of the system 1232, and a variety of digital I/O interfaces 1222 to the station's motor and sensors.

The power conditioning circuitry 1240 converts the +24V DC supplied by the shared bus 214 to the voltages and current levels needed by the subsystem's electronics, sensors and actuators, typically +5V, +15V and −15V. This conversion is best made by a low-dissipation, high-efficiency DC-DC converter or other acceptable means.

The processor group 1212 contains a general purpose microprocessor 1214 with the following specifications: 16-bit word length, clock speed of at least 30 MHz, at least 64 Kbytes of non-volatile FLASH program memory 1216, at least 16 Kbytes of data RAM 1218, an expanded address/data bus interface, SPI and UART serial interface 1220 to diagnostic RS-232 I/O port 1226, and a multi-bit digital I/O interface 1222. The processor's digital I/O interface 1222 controls the various motors of the station: (1) the Output Element elevator motor 1228 through stepper/servo motor drivers 1224 and position/velocity decoder 1230 in order to position the support housings to the plane of the carousel transport mechanism; and (2) the Output Element loader motor 1236 through stepper/servo motor drivers 1234 and position/velocity decoder 1238 in order to transfer support housings from the Carousel Holding Device to the Output Element. Communication with other station controllers is supported through the intra-wash station network I/O interface 1232 via buses 206 and 208. This controller module is also linked to the Control Processor 200 through an IEEE Std-1149 JTAG scan bus 208. The JTAG bus supports down loading of software into the station control processor and it supports hardware diagnostics. Processor 1214 is governed by embedded real-time executive and application-specific software to control the required tasks and operation activity of the station.

In summary, System Architecture 3 is a modular design in which control of the apparatus is distributed among several microprocessor control modules. This architecture provides (1) supervision of semi-autonomous subsystem modules by a centralized Control Processor module, (2) common shared buses over which multiple control modules intercommunicate and interact with each other, (3) multiple instances of microprocessor-based control modules each dedicated to controlling one station of the apparatus, (4) over-all control system extendibility and expandability through the addition of modules to the common buses.

EXAMPLES

The invention is demonstrated further by the following illustrative examples. The following examples are by way of illustration and not limitation. The apparatus and methods of the invention may be employed in many processing protocols including wash protocols as will be apparent to those skilled in the art in view of the above disclosure.

In-situ synthesized 25-mer oligonucleotide arrays containing 8455 features were fabricated by appropriate procedures on 1-mm thick glass and diced to 22×22-mm die. Each die was packaged as described in U.S. patent application Ser. No. 09/299,976, filed Apr. 27, 1999. The arrays contained 4×-replicated, optimized probes against human reference sequence genes (RefSeq). Three sequences were used per gene, for a total of 12 probes per gene. The array included a variety of positive and negative control probes. The probes were arranged into 4 identical quadrants on the die. A fluorescently labeled mRNA sample from K562 cells was injected into each packaged array. The sample quantity was 250 μL. The packaged arrays were hybridized by incubation overnight at 60° C. During incubation, the contents of the packaged arrays were bubble mixed by package rotation.

At the end of the hybridization period, the packaged arrays were removed from the incubator and cooled to room temperature conditions. The lid was then removed and each packaged array was washed using the protocol shown below on an apparatus essentially equivalent to the fluid dispensing stations of the present invention, the structure and operation of which is described above. This apparatus, functionally equivalent to the First (and Second) Fluid Dispensing stations and the intervening mixing station, was constructed to verify only the wash process concepts and to test the fluidics design and wash protocol timing. This test apparatus did not include: an Input Element, Lid Removal station, Carousel, Spin Dryer and Output Element.

The apparatus comprised a plate to locate each packaged array oriented with the array facing up, means to control the temperature of the packaged array, fluid dispensing stations comprising a fluid feed tube and fluid aspiration tube that could be raised and lowered into the well of the packaged array where the array forms the bottom of the well, fluid supply containers, fluid waste containers, pressure source and control valves and software to control the system.

The apparatus used a pressurized source fluid bottle feeding a length of 1/16 inch OD, 0.03 inch ID Teflon tubing. The pressure for the source bottle was derived from a house nitrogen source at about 60 psi regulated down to the desired pressure. The following table shows the wash fluid flow rates and source bottle pressures that were used in the apparatus. It should be noted that the length of tubing and the viscosity of the wash fluid affected the flow rate for a given pressure in the source bottle. The more important parameter is the flow rate and not the pressure required. Accordingly, if a different tubing system or different viscosity wash fluid were to be used, routine testing with different pressures may be made to get the desired flow rate.

| Source Bottle Pressure (psi) | Wash Fluid Flow Rate (ml/minute) |
| --- | --- |
| 12 | 87 |
| 9 | 72 |
| 6 | 53 |
| 3 | 36 |
| 1.5 | 23 |

Waste fluids were aspirated to a storage bottle through a length of 1/8 inch OD, 0.0625 inch ID Teflon tubing by vacuum. The vacuum was supplied by a house vacuum source with waste bottle at about −20 inches of mercury. The height above the array surface of the ends of the wash fluid source and waste aspiration tubes was adjustable. The height of the waste tube was adjusted so that, when the package was filled with fluid and then aspirated, a film of fluid was left over the array. The height of the waste tube can also control the mixing effect when both the wash dispense and waste aspiration were activated. The height adjustment depended on the vacuum achieved at the end of the waste tube. The end of the tube for the wash fluid dispense was bent with a ¼ inch radius 90 degrees to redirect the fluid flow across the array and maximize the washing/mixing effect. The height of the tube was set to provide the optimum mixing effect. The wash apparatus allowed for dispensing wash fluid into the array package as well as aspirating the waste out of the package. The dispense and aspiration had independent on/off controls to allow these combinations:

| Dispense | Aspirate | Function |
| --- | --- | --- |
| Off | Off | No action/Soak |
| On | Off | Fill package |
| On | On | Mix and remove waste |
| Off | On | Empty package |

Each protocol used a sequence of these states to fill the opened array package, mix and wash the package and empty the package. The amount of wash fluid dispensed to the package was controlled by the time the valve was on. The amount of fluid required to wet to bottom of the package completely depended on the viscosity and quantity of the fluid already in the package, the viscosity of the wash fluid being added to the package, and the amount of surfactant present. The timing of the valves was changed during the course of some of the protocols to compensate for the changing viscosity/surfactant level of the fluid as the sample is removed. It was desirable to initially fill with the smallest amount of fluid as possible that completely wet the bottom of the package to prevent washing high concentration sample up the walls of the package. Later fills used more volume in order to wash higher up the walls of the package. The bottom of the package was completely wetted before the aspiration was started in order to get the best mixing/washing effect.

The wash experiments on the arrays used 6 psi (flow rate approximately 53 mL/min) for all of the different wash protocols. Each wash experiment consisted of four wash steps: Protocol 1, a second repeated instance of Protocol 1, Protocol 2, and concluded with Protocol 3. Each of these protocols is described below.

---

Protocol 1 (6 psi): Dilute sample by filling and draining for 47 seconds.

Wash fluid:

6x SSC and room temperature
(0.9 M Sodium Chloride and 0.09 M Sodium Citrate, available from Amresco, Solon, OH)
6 Fill/wash/drain cycles as follows:

1-Fill about 0.9 ml, wash with about 9 ml, then drain
2-Fill about 2 ml, wash with about 2.6 ml, then drain
3-Fill about 2.6 ml, wash with about 2.6 ml, then drain
4–#6-Fill about 3.7 ml, wash with about 2.6 ml, then drain
1 Final fill/drain cycle as follows:

Fill about 2.6 ml, then drain.

---

Protocol 2 (10 min, 6 psi): Fill and Drain every 30 second for 10 minutes

Wash fluid:

6x SSC and room temperature
(0.9 M Sodium Chloride and 0.09 M Sodium Citrate, available from Amresco, Solon, OH)
20 Fill/wash/soak/drain cycles as follows:

1–#20-Fill about 3.7 ml, wash with about 2.6 ml, fill about 0.9 ml, soak for 12 second, then drain
1 Final fill/drain cycle as follows:

Fill about 2.6 ml, then drain

---

Protocol 3 (5 min, 6 psi): Fill and Drain every 60 second for 5 minutes, Cold 0.1x SSC Wash fluid:

0.1x SSC and about 6° C.
(0.015 M Sodium Chloride and 0.0015 M Sodium Citrate, available from Amresco, Solon, OH)
5 Fill/wash/soak/drain cycles as follows:

1–#5-Fills about 3.7 ml, wash with about 2.6 ml, fill about 1.2 ml, soak for 42 second, then drain.
1 Final fill/drain cycle as follows:

Fill about 2.6 ml, then drain

---

After all of the wash steps were completed, the packaged arrays were spun dry at 1800 rpm for 30 seconds and then removed from the apparatus to a scanner, where the arrays were scanned for fluorescent signal. The results were comparable to manually processed arrays in signal and background levels.

All publications, patents and patent applications cited in this specification are herein incorporated by reference as if each individual publication, patent or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An apparatus comprising:
   (a) an input element, the input element comprising a plurality of shelves, the input element being adapted to move the shelves vertically in a predetermined manner to receive packages into the apparatus and move the packages to a holding device therefor,
   (b) a movably mounted holding device for holding a plurality of support housings, said device being adapted to receive a support housing from said input element and adapted to index each support housing for a predetermined operation, each of said support housings comprising a cover and containing a support having attached thereto a plurality of biopolymer features,
   (c) an element for removing the cover from the support housing to expose an opening in the support housing,
   (d) one or more processing stations, and
   (e) an output element adapted to receive a support housing from said holding device, the output element comprising a plurality of shelves, the output element being adapted to move the shelves vertically in a predetermined manner to receive a package from the holding device.

2. An apparatus according to claim 1 wherein the input element is adapted to be indexed.

3. An apparatus according to claim 1 wherein the output element is adapted to be indexed.

4. An apparatus according to claim 1 further comprising an element for identifying each of the supports.

5. An apparatus according to claim 4 wherein the element comprises a bar code reader associated with the input element.

6. An apparatus according to claim 1 further comprising a device for physically removing unbound materials from the surface of a support within each of the support housings, the device being adapted for receiving a support from the holding device.

7. An apparatus according to claim 1 wherein said processing stations are fluid dispensing station(s) that dispense and remove fluids.

8. An apparatus according to claim 1 further comprising means for mixing the fluid on the surface of a support within each of the support housings.

9. An apparatus according to claim 1 further comprising a central microprocessor-based or microcontroller-based module connected to a plurality of interface modules for controlling elements (a)–(d).

10. An apparatus according to claim 1 further comprising a plurality of microprocessor-based or microcontroller-based modules for controlling elements (a)–(d), each comprising an individual architectural design and software wherein the individual architectural design and the software are adapted specifically to control a function that each of the modules serves.

11. An apparatus according to claim 1 wherein the input element is temperature controlled.

12. An apparatus comprising:
   (a) an input element, the input element comprising a plurality of package holders in the form of shelves, the input element being adapted to move the shelves vertically in a predetermined manner to receive packages into the apparatus and move the packages to a holder therefor, (b) a circuitous transport for holding a plurality of packages, each of which contains a support, the surface of which has attached thereto a plurality of polynucleotide features, the circuitous transport being adapted to receive a package from the input element and adapted to index each package for a predetermined operation, (c) an element for identifying each of the packages, (d) an element for introducing fluid into and removing fluid from the packages, (e) one or more fluid dispensing stations adapted to dispense fluids to, and aspirate fluids from, the supports in the packages on said circuitous transport, (f) a device for physically removing unbound materials from the surface of a support within each of the packages, the device being adapted for receiving a package from the circuitous transport, and (g) an output element adapted to receive a package from the circuitous transport, the output element comprising a plurality of package holders in the form of shelves, the output element being adapted to move the shelves vertically in a predetermined manner to receive packages from the circuitous transport.

13. An apparatus according to claim 12 wherein the packages are covered and the element for accessing the package is a device for removing the cover.

14. An apparatus according to claim 12 wherein the input element or the output element is adapted to be indexed.

15. An apparatus according to claim 12 wherein the element for identifying each of the packages comprises a bar code reader associated with the input element.

16. An apparatus according to claim 12 wherein the device of (f) is adapted to remove unbound materials by an applied force.

17. An apparatus according to claim 12 further comprising a central microprocessor-based or microcontroller-based module connected to a plurality of interface modules for controlling elements (a)–(g).

18. An apparatus according to claim 12 further comprising a plurality of microprocessor-based or microcontroller-based modules for controlling elements (a)–(g), each comprising an individual architectural design and software wherein the individual architectural design and the software are adapted specifically to control a function that each of the modules serves.

19. An apparatus according to claim 12 wherein said circuitous transport is a circular tray.

20. An apparatus comprising:

(a) an input element mounted on a frame, the input element comprising a plurality of shelves, the input element being adapted to move the shelves vertically in a predetermined manner to receive packages into the apparatus and move the packages to a holder therefor, the input element being adapted for temperature control, (b) a circular tray for holding a plurality of packages, each of which contains a support, the surface of which has attached thereto a plurality of polynucleotide features, the circular tray being movably mounted on the frame and being adapted to receive a package from the input element and adapted to index each package for a predetermined operation, each of the packages comprising a cover and an identification code, (c) a device, mounted on the frame, for reading the identification code on each of the packages, (d) a device, mounted on the frame, for removing the cover on each of the packages to expose an opening thereof, (e) one or more fluid dispensing stations mounted on the frame and adapted to dispense fluids to, and aspirate fluids from, the supports in the packages on the circular tray, (f) a device adapted to remove unbound materials on the surface of a support within each of the packages, the device being mounted on the frame and adapted for receiving a package from the circular tray, (g) an output element mounted on the frame and adapted to receive a package from the circular tray, the output element comprising a plurality of shelves, the output element being adapted to move the shelves vertically in a predetermined manner to receive a package from the circular tray, and (h) a central microprocessor-based or microcontroller-based module connected to a plurality of interface modules for controlling elements (a)–(g).

21. An apparatus according to claim 20 wherein the input element is an elevator system.

22. An apparatus according to claim 20 wherein the output element is an elevator system.

23. An apparatus according to claim 20 wherein the microprocessor-based or microcontroller-based modules each comprise an individual architectural design and software wherein the individual architectural design and the software are adapted specifically to control a function that each of the modules serves.

24. A method for processing a plurality of samples each of which are present on a support contained within a support housing comprising a cover, the method comprising:

(a) moving each of the support housings to a holder therefor and moving said holder to one or more fluid dispensing stations, wherein the surface of each of the supports comprises a plurality of biopolymer features and wherein said support housings are moved on shelves vertically in a predetermined manner to receive said support housings and to move said support housings and wherein the location and identity of each of the support housings is indexed, (b) removing the cover of each of the support housings, (c) applying fluid to the surface of each of the supports at the fluid dispensing stations for processing the samples, (d) aspirating fluid from the surface of each of the supports at the fluid dispensing stations, (e) moving each of the support housings away from the fluid dispensing stations, (f) physically removing residual fluid from each of the supports within the support housings, and (g) moving each of the support housings away from said processing wherein said support housings are received onto and moved on shelves vertically in a predetermined manner.

25. A method according to claim 24 wherein the processing is washing.

26. A method according to claim 24 wherein the supports are present on a movable tray.

27. A method according to claim 26 wherein the movable tray is a circular tray.

28. A method according to claim 24 wherein the step of physically removing fluid from each of the supports is accomplished by applying a force thereto.

29. A method for processing a plurality of samples each of which are present on a support contained in a covered package, the method comprising:

(a) moving each of the covered packages from an input element to a movable holding device for holding a plurality of the covered packages, wherein the surface of each of the supports comprises a microarray of polynucleotide features and wherein the input element provides temperature control and movement of the covered packages vertically to the movable holding device and wherein the location and identity of each of the covered packages is continuously indexed, (b) moving the holding device in an indexed manner to move the covered packages to a device for removing covers from the covered packages, (c) moving the holding device in an indexed manner to deliver each of the packages to one or more fluid dispensing stations, (d) moving the holding device to deliver each of the packages to a device for physically removing unbound materials from the surface of each of the supports, (e) moving the holding device in an indexed manner to deliver each of the packages to an output element and (f) moving the packages vertically in the output element to remove the packages from said processing.

30. A method according to claim 29 wherein the covered packages in step (a) are moved to the holding device from an input element comprising a plurality of shelves.

31. A method according to claim 29 wherein the output element comprises a plurality of shelves.

32. A method according to claim 29 wherein the covered packages in step (a) are moved to the holding device past an element for identifying each of the packages.

33. A method according to claim 32 wherein the element for identifying each of the packages comprises a bar code reader associated with the input element.

34. A method according to claim 29 wherein the device of step (d) is a device in which a force is applied to the unbound materials.

35. A method according to claim 29 wherein said moving steps (a)–(f) are controlled by a central microprocessor-based or microcontroller-based module connected to a plurality of interface modules.

36. A method according to claim 29 wherein said moving steps (a)–(f) are controlled by a plurality of microprocessor-based or microcontroller-based modules, each comprising an individual architectural design and software wherein the individual architectural design and the software are adapted specifically to control a function that each of the modules serves.

37. A method according to claim 29 further comprising subsequent to step (f) examining the surface of each of the supports for the results of the processing of the samples.

38. A method according to claim 37 further comprising transmitting the results of the processing to a remote location.

39. An apparatus comprising:

(a) a frame, (b) an input element affixed to the frame, the input element comprising a plurality of shelves, the input element being adapted to move the shelves vertically in a predetermined manner to receive packages into the apparatus and move the packages to a holding device therefor, (c) a holding device for holding a plurality of support housings, the device being adapted to receive a support housing from the input element and adapted to index each support housing for a predetermined operation, the device being movably mounted on the frame, each of the support housings comprising a cover and containing a support having attached thereto a plurality of biopolymer features, (d) an element for removing said covers to expose an opening in said support housings, (e) one or more fluid dispensing stations affixed to the frame, and (f) an output element affixed to the frame, the output element being adapted to receive a support housing from the holding device, the output element comprising a plurality of shelves, the output element being adapted to move the shelves vertically in a predetermined manner, wherein said elements (b)–(e) are each controlled by a central microprocessor-based or microcontroller-based module connected to a plurality of interface modules, wherein the modules are interconnected by a multi-channel shared bus originating at and supervised by a system controller, which interfaces with a front panel display and operator controls.

40. An apparatus according to claim 39 wherein said bus makes available to each of said elements: (i) isolated 120V AC power, (ii) common system control signals, (iii) IEEE Std 1194 JTAG scan bus signals, (iv) intra-apparatus data communications network, (v) in-circuit programming, and (vi) DC power.

41. An apparatus comprising:

(a) a frame, (b) an input element affixed to the frame, the input element comprising a plurality of shelves, the input element being adapted to move the shelves vertically in a predetermined manner to move the support housings into the apparatus and move the support housings to a holding device, (c) a holding device for holding a plurality of support housings, the device being adapted to receive a support housing from the input element and adapted to index each support housing for a predetermined operation, the device being movably mounted on the frame, each of the support housings containing a support having attached thereto a plurality of biopolymer features, (d) one or more fluid dispensing stations affixed to the frame, and (e) an output element affixed to the frame, the output element being adapted to receive a support housing from the holding device, the output element comprising a plurality of shelves, the output element being adapted to move the shelves vertically in a predetermined manner to receive a support housing from the holding device, wherein each of said elements (b)–(e) are controlled by one of a plurality of microprocessor-based or microcontroller-based modules, each comprising an individual architectural design and software wherein the individual architectural design and the software are adapted specifically to control a function that each of the modules serves, wherein the modules are interconnected by a multi-channel shared bus originating at and supervised by a central system controller, which interfaces with a front panel display and operator controls.

42. An apparatus according to claim 41 wherein said bus makes available to all of said modules: (i) common system control signals, (ii) IEEE Std 1194 JTAG scan bus signals, (iii) intra-apparatus data communications network, (iv) in-circuit programming bus, and (v) regulated DC power.

43. An apparatus according to claim 41 wherein said plurality of modules comprise (i) a central system controller, (ii) a communications interface controller, (iii) a system power supply, (iv) a temperature controller, (v) a fluid and valve controller and (vi) a motion/motor controller.

* * * * *